United States Patent
Sone et al.

(10) Patent No.: US 11,331,147 B2
(45) Date of Patent: May 17, 2022

(54) MEDICAL IMAGE PROCESSING APPARATUS, MEDICAL IMAGE DIAGNOSTIC APPARATUS, AND MEDICAL IMAGE PROCESSING METHOD FOR IMAGE-GUIDED ENDOCARDIAL NAVIGATION

(71) Applicant: CANON MEDICAL SYSTEMS CORPORATION, Otawara (JP)

(72) Inventors: Yukari Sone, Nasushiobara (JP); Kazumasa Arakita, Utsunomiya (JP); Takahiko Nishioka, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 588 days.

(21) Appl. No.: 16/021,644

(22) Filed: Jun. 28, 2018

(65) Prior Publication Data

US 2019/0000551 A1 Jan. 3, 2019

(30) Foreign Application Priority Data

Jun. 30, 2017 (JP) .............................. JP2017-129616

(51) Int. Cl.
*A61B 34/00* (2016.01)
*A61B 34/10* (2016.01)
(Continued)

(52) U.S. Cl.
CPC .............. *A61B 34/10* (2016.02); *A61B 6/032* (2013.01); *A61B 6/12* (2013.01); *A61B 6/463* (2013.01);
(Continued)

(58) Field of Classification Search
CPC ... A61B 2034/107; A61B 34/10; A61B 6/032; A61B 6/12; A61B 6/463; A61B 6/466;
(Continued)

(56) References Cited

U.S. PATENT DOCUMENTS

| | | | |
|---|---|---|---|
| 2004/0220462 A1* | 11/2004 | Schwartz | ............... A61B 5/287 600/374 |
| 2007/0032826 A1 | 2/2007 | Schwartz | |
| 2008/0172049 A1* | 7/2008 | Bredno | .............. A61B 18/1492 606/29 |
| 2008/0234576 A1 | 9/2008 | Gavit-Houdant et al. | |

(Continued)

FOREIGN PATENT DOCUMENTS

| | | | | |
|---|---|---|---|---|
| JP | 2016-512726 A | 5/2016 | | |
| WO | WO-2017102898 A1 * | 6/2017 | ............. | A61B 34/10 |

OTHER PUBLICATIONS

Japanese Office Action dated Mar. 30, 2021 Japanese Patent Application No. 2017-129616, 4 pages.

(Continued)

*Primary Examiner* — Keith M Raymond
*Assistant Examiner* — Adam D. Kolkin
(74) *Attorney, Agent, or Firm* — Oblon, McClelland, Maier & Neustadt, L.L.P.

(57) ABSTRACT

A medical image processing apparatus according to an embodiment comprises processing circuitry configured to: acquire a position of an interatrial septum and a device reaching position in a medical image indicating the heart of a subject; calculate a puncturing region, in the interatrial septum, enabling a medical device to reach the device reaching position through the interatrial septum on the basis of the position of the interatrial septum and the device reaching position; and present the puncturing region.

19 Claims, 17 Drawing Sheets

(51) Int. Cl.
*A61B 8/00* (2006.01)
*A61B 6/03* (2006.01)
*G06T 7/00* (2017.01)
*A61B 6/00* (2006.01)
*A61B 6/12* (2006.01)
*A61B 8/08* (2006.01)

(52) U.S. Cl.
CPC .............. *A61B 6/466* (2013.01); *A61B 6/503* (2013.01); *A61B 6/5235* (2013.01); *A61B 6/5247* (2013.01); *A61B 8/466* (2013.01); *G06T 7/0012* (2013.01); *A61B 8/0883* (2013.01); *A61B 8/483* (2013.01); *A61B 2034/107* (2016.02); *G06T 2207/10081* (2013.01); *G06T 2207/30048* (2013.01)

(58) Field of Classification Search
CPC ..... A61B 6/503; A61B 6/5235; A61B 6/5247; A61B 8/0883; A61B 8/466; A61B 8/483; G06T 2207/10081; G06T 2207/30048; G06T 7/0012
See application file for complete search history.

(56) References Cited

U.S. PATENT DOCUMENTS

| | | | |
|---|---|---|---|
| 2011/0190624 A1* | 8/2011 | Cinbis | A61B 5/0084 600/424 |
| 2014/0037049 A1* | 2/2014 | Langan | A61B 6/541 378/20 |
| 2014/0142422 A1* | 5/2014 | Manzke | A61B 1/00149 600/424 |
| 2014/0187921 A1* | 7/2014 | Nakada | A61B 6/461 600/424 |
| 2015/0011886 A1* | 1/2015 | Radulescu | A61B 8/585 600/447 |
| 2017/0181795 A1* | 6/2017 | Debruyne | A61B 18/24 |
| 2018/0085167 A1* | 3/2018 | Goyal | A61B 34/00 |

OTHER PUBLICATIONS

Kajiyama, Y., et al., "Efficacy of Multi-detector CT and Transesophageal Echocardiography for Transseptal Catheter Ablation of Congenital Heart Disease", Pediatric Cardiology and Cardiac Surgery, vol. 24, No. 5, pp. 640-646 (with English abstract and partial English translation).

* cited by examiner

MEDICAL IMAGE PROCESSING APPARATUS, MEDICAL IMAGE DIAGNOSTIC APPARATUS, AND MEDICAL IMAGE PROCESSING METHOD FOR IMAGE-GUIDED ENDOCARDIAL NAVIGATION

CROSS-REFERENCE TO RELATED APPLICATIONS

This application is based upon and claims the benefit of priority from Japanese Patent Application No. 2017-129616, filed on Jun. 30, 2017; the entire contents of which are incorporated herein by reference.

FIELD

Embodiments described herein relate generally to a medical image processing apparatus, a medical image diagnostic apparatus, and a medical image processing method.

BACKGROUND

In prior art, in an operation on the heart, a medical device running through a blood vessel and reaching the heart is used. Such a medical device is formed of various devices, such as a catheter, and is bendable in the blood vessel of the subject. In an operation using such a medical device, for example, first, the catheter reaches the heart along a preceding guide wire. Thereafter, the device corresponding to the purpose of the operation reaches the heart through the inside of the catheter, to perform an operation on the heart. This avoids thoracotomy in an operation on the heart, and reduces a burden on the subject.

In some positions of a treatment target region in the heart, the medical device may puncture an interatrial septum, to reach the treatment target region. For example, when the treatment target region exists in the left atrium, the medical device is inserted from the femoral vein of the subject, and punctures the interatrial septum from the right atrium side to reach the treatment target region.

In some positions where the medical device punctures the interatrial septum, there are cases where the medical device does not reach the treatment target region. Specifically, although the medical device is bendable, its bending angle or the like is restricted, there are cases where the medical device cannot reach the treatment target region, in some positional relations between the puncturing position and the treatment target region. In addition, in some puncturing positions of the medical device in the interatrial septum, there are cases where the medical device contacts the heart, before the medical device reaches the treatment target region. Besides, the interatrial septum includes positions that are thick and difficult to puncture, and/or positions at which the medical device may hurt the aorta when puncturing. The operator of the medical device empirically determines the puncturing position in the interatrial septum, in consideration of these circumstances. In addition, although the medical device has punctured the interatrial septum, when the medical device does not reach the treatment target region, there are cases where an operation with the medical device is abandoned, and the operation is changed to a surgical operation, such as thoracotomy.

DETAILED DESCRIPTION

A medical image processing apparatus according to an embodiment comprises processing circuitry. The processing circuitry is configured to acquire a position of an interatrial septum and a device reaching position in a medical image indicating the heart of a subject. The processing circuitry is also configured to calculate a puncturing region, in the interatrial septum, enabling a medical device to reach the device reaching position through the interatrial septum on the basis of the position of the interatrial septum and the device reaching position. The processing circuitry is further configured to present the puncturing region.

The following is a detailed explanation of embodiments of the medical image processing apparatus, a medical image diagnostic apparatus, and a medical image processing method, with reference to the drawings First, a first embodiment will be described hereinafter. The first embodiment illustrates a medical image processing system including the medical image processing apparatus, as an example.

Figure 1:
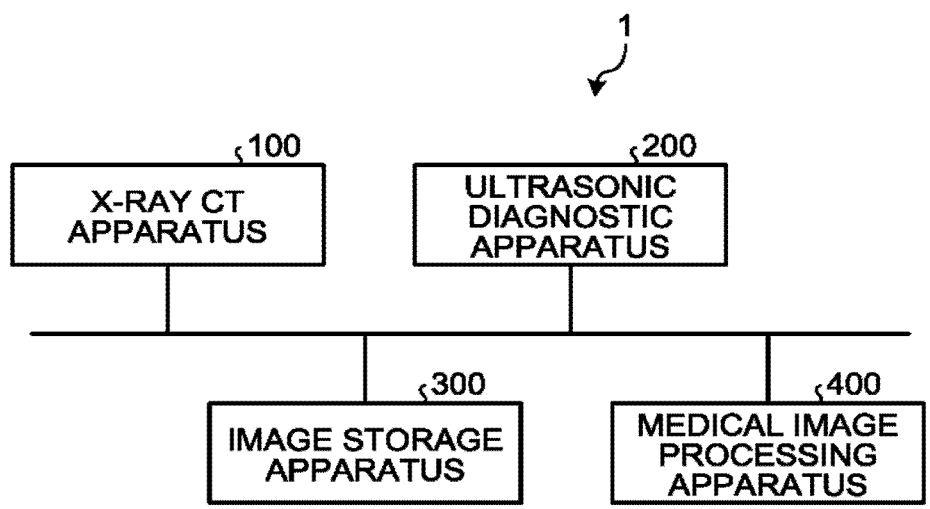
FIG. 1 is a diagram illustrating an example of a medical image processing system according to a first embodiment.

FIG. 1 is a diagram illustrating an example of a medical image processing system 1 according to the first embodiment. As illustrated in FIG. 1, the medical image processing system 1 according to the first embodiment includes an X-ray CT apparatus 100, an ultrasonic diagnostic apparatus 200, an image storage apparatus 300, and a medical image processing apparatus 400. The X-ray CT apparatus 100, the ultrasonic diagnostic apparatus 200, the image storage apparatus 300, and the medical image processing apparatus 400 are mutually connected through a network.

The X-ray CT apparatus 100 is an apparatus acquiring CT image data from a subject P (not illustrated). For example, the X-ray CT apparatus 100 executes scan of the subject P to acquire CT image data indicating the heart of the subject P. In addition, the X-ray CT apparatus 100 displays a CT image based on the acquired CT image data. The X-ray CT apparatus 100 is an example of a medical image diagnostic apparatus acquiring a medical image from the subject P. For example, the medical image processing system 1 may acquire a medical image with another medical image diagnostic apparatus, such as a magnetic resonance imaging (MRI) apparatus, instead of the X-ray CT apparatus 100.

The ultrasonic diagnostic apparatus 200 is an apparatus acquiring ultrasonic image data from the subject P. For example, the ultrasonic diagnostic apparatus 200 performs scan with a transesophageal echocardiography (TEE) probe in a state of abutting against the upper digestive tracts (such as the esophagus and the stomach) of the subject P to image a region including the heart of the subject P. The ultrasonic diagnostic apparatus 200 also displays the actually imaged ultrasonic image. The term "actually imaged ultrasonic image" indicates an ultrasonic image promptly displayed after imaging. In other words, the ultrasonic diagnostic apparatus 200 displays an ultrasonic image in real time. This enables the operator who performs an operation to perform the operation on the heart while referring to the heart of the subject P and the medical device inserted into the heart.

The medical device is a device reaching a device reaching position, such as the treatment target region, in the heart, through the interatrial septum. For example, the medical device is formed of a catheter, a guide wire, and a needle (puncture needle), and the like. The catheter is a bendable tube, and a guide wire and a needle and the like can be inserted through the inside thereof. The guide wire is line-shaped metal guiding advance of the catheter. The needle is a needle puncturing the interatrial septum to cause the medical device to puncture the interatrial septum.

For example, the guide wire is inserted from the femoral vein of the subject P, and reaches the right atrium of the subject P. Thereafter, the catheter reaches the right atrium of the subject P along the preceding guide wire. Thereafter, the needle runs through the catheter to reach the right atrium of the subject P and punctures the interatrial septum. Specifically, the needle punctures an oval fossa (region after the oval foramen is closed). Thereafter, the guide wire is inserted into the left atrium from the position punctured with the needle. The catheter runs along the preceding guide wire to reach the left atrium of the subject P. The device corresponding to the purpose of the operation reaches the left atrium of the subject P through the inside of the catheter to perform the operation on the heart.

Examples of a device corresponding to the purpose of the operation include a clip-shaped device clipping the distal end of the mitral valve in the treatment of mitral insufficiency. Such a clip-shaped device clips the distal end of the mitral valve to release or solve a backward flow of the blood due to insufficient closure. In the following description, such a clip-shaped device is simply referred to as "clip". In this case, the medical device also includes a clip, in addition to the catheter, the guide wire, and the needle.

For example, after the catheter reaches the left atrium, the clip reaches the left atrium of the subject P through the inside of the catheter, and is held at the distal end position of the catheter. Thereafter, the catheter is bent in accordance with an instruction of the operator. In this manner, the clip at the distal end position of the catheter moves to the distal end position of the mitral valve. Thereafter, the clip clips two valves forming the mitral valve to bring them in contact with each other. The clip is indwelled in a state of holding the distal end of the mitral valve, and the catheter, the guide wire, and the needle are extracted out of the subject P. The hole in the oval fossa formed by puncturing with the medical device can be covered with a button-shaped device when the catheter, the guide wire, and the needle are extracted out of the subject P.

Another example of a device corresponding to the purpose of the operation is an umbrella-shaped device used in the left atrial appendage closure. Such an umbrella-shaped device closes the left atrial appendage to prevent diseases caused by a thrombus formed in the left atrial appendage. In the following description, such an umbrella-shaped device will be simply referred to as "umbrella-shaped device". In this case, the medical device includes an umbrella-shaped device, in addition to the catheter, the guide wire, and the needle.

For example, after the catheter reaches the left atrium, the catheter is bent such that the distal end thereof is disposed in the left atrial appendage. Thereafter, the umbrella-shaped device reaches the left atrium of the subject P through the inside of the catheter, and is held at the distal end position (that is, inside the left atrial appendage). Thereafter, the umbrella-shaped device is transformed to spread inside the left atrial appendage and close the left atrial appendage, and is indwelled in a state of closing the left atrial appendage. The catheter, the guide wire, and the needle are extracted out of the subject P, while the hole of the oval fossa is covered with a button-shaped device.

The clip used for an operation on the mitral valve and the umbrella-shaped device used for an operation on the left atrial appendage have been explained as examples of a device corresponding to the purpose of the operation, but the embodiments are not limited thereto. For example, the device corresponding to the purpose of the operation may be a device used for an operation on a region (such as the left ventricle and the aortic valve) located in a more downstream direction of the blood than the left atrium.

In FIG. 1, the image storage apparatus 300 is an apparatus storing CT image data acquired with the X-ray CT apparatus 100. For example, the image storage apparatus 300 is achieved with a computer apparatus, such as a server apparatus. As an example, the image storage apparatus 300 receives CT image data from the X-ray CT apparatus 100 through the network. In addition, the image storage apparatus 300 creates databases and manages the received CT image data.

The medical image processing apparatus 400 acquires CT image data through the network, and executes various processing using the acquired CT image data. For example, the medical image processing apparatus 400 is achieved with a computer apparatus, such as a workstation. In the present embodiment, the medical image processing apparatus 400 acquires CT image data from the X-ray CT apparatus 100 or the image storage apparatus 300 through the network. The medical image processing apparatus 400 also calculates the puncturing region of the medical device on the basis of the acquired CT image data, and presents the calculated puncturing region to the operator. The puncturing region will be described later.

Figure 2:
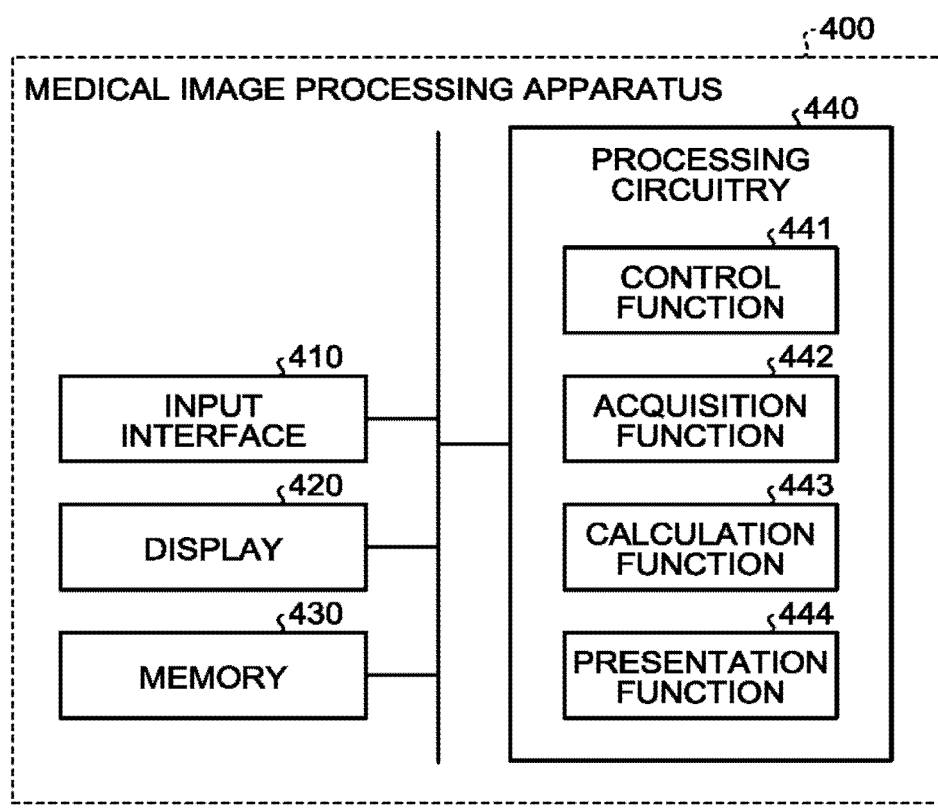
FIG. 2 is a block diagram illustrating an example of a medical image processing apparatus according to the first embodiment.

The following is an explanation of an example of the medical image processing apparatus 400 with reference to FIG. 2. FIG. 2 is a block diagram illustrating an example of the medical image processing apparatus 400 according to the first embodiment. As illustrated in FIG. 2, the medical image processing apparatus 400 includes an input interface 410, a display 420, a memory 430, and processing circuitry 440.

The input interface 410 includes a mouse, a keyboard, a track ball, a switch, a button, a joy stick, and/or a touch panel and the like used by the operator for inputting various instructions and/or various settings, and transmits information of the instruction and/or the setting received from the operator to the processing circuitry 440.

The display 420 is a monitor referred to by the operator. The display 420 presents various medical images to the operator, under the control of the processing circuitry 440, and displays graphical user interface (GUI) to receive various instructions and/or various settings from the operator through the input interface 410.

The memory 430 is a nonvolatile storage device, such as a semiconductor memory device, such as a flash memory, a hard disk, and an optical disk. For example, the memory 430 stores CT image data acquired from the X-ray CT apparatus 100 or the image storage apparatus 300. The memory 430 also stores therein a computer program to achieve functions described later with the processing circuitry 440.

The processing circuitry 440 executes a control function 441, an acquisition function 442, a calculation function 443, and a presentation function 444 to control operations of the whole medical image processing apparatus 400. For example, the processing circuitry 440 reads a computer program corresponding to the control function 441 from the memory 430 and executes the computer program to receive various instructions and/or settings from the operator through the input interface 410.

In addition, for example, the processing circuitry 440 reads a computer program corresponding to the acquisition function 442 from the memory 430 and executes the computer program to acquire the position of the interatrial septum and the device reaching position from the CT image data.

The following description illustrates the case of acquiring an oval fossa region corresponding to the oval fossa, in the position of the interatrial septum, as an example. The following description illustrates a target region corresponding to the treatment target region, as an example of the device reaching position. Specifically, the following description illustrates the case of acquiring the oval fossa region corresponding to the oval fossa and the target region corresponding to the treatment target region from the CT image data.

In addition, for example, the processing circuitry 440 reads computer programs corresponding to the calculation function 443 and the presentation function 444 from the memory 430 and executes the computer programs to calculate the puncturing region through which the medical device punctures in the interatrial septum of the subject P, and present the calculated puncturing region to the operator. Calculation and presentation of the puncturing region will be described later.

In the medical image processing apparatus 400 illustrated in FIG. 2, each of the processing functions is stored in the form of a computer program executable with a computer in the memory 430. The processing circuitry 440 is a processor that reads the computer program from the memory 430 and executes the computer program to achieve the function corresponding to the computer program. In other words, the processing circuitry 440 in the state of having read the computer program has functions corresponding to the read computer program. FIG. 2 illustrates that the single processing circuitry 440 achieves the control function 441, the acquisition function 442, the calculation function 443, and the presentation function 444, but a plurality of independent processors may be integrated to form the processing circuitry 440, and the processors may perform the respective computer programs to achieve the functions.

The configuration of the medical image processing system 1 has been described above. With the configuration, the medical image processing apparatus 400 in the medical image processing system 1 facilitates an operation with puncturing of the interatrial septum. Specifically, with the process performed with the processing circuitry 440 described in detail hereinafter, the medical image processing apparatus 400 calculates the puncturing region to enable the medical device to reach the treatment target region, on the basis of CT image data, and presents the calculated puncturing region to facilitate an operation with puncturing of the interatrial septum. The following is a detailed explanation of the process performed with the medical image processing apparatus 400 according to the first embodiment.

Figure 3:
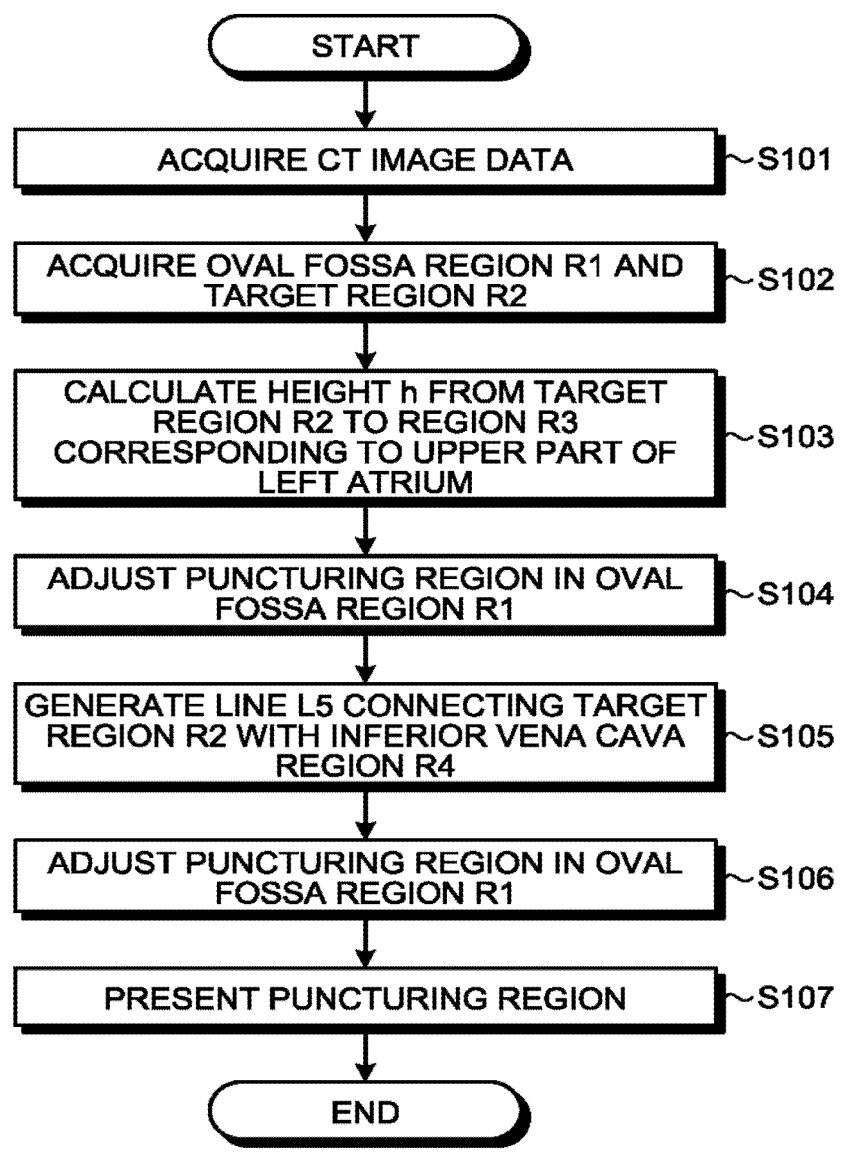
FIG. 3 is a flowchart for explaining a flow of a process of the medical image processing apparatus according to the first embodiment.

The following is an explanation of an example of the process performed with the medical image processing apparatus 400, with reference to FIG. 3. FIG. 3 is a flowchart for explaining a flow of the process of the medical image processing apparatus 400 according to the first embodiment. The following explanation illustrates treatment of mitral insufficiency, as an example. In this case, the medical device includes a catheter, a guide wire, a needle, and a clip.

First, as illustrated in FIG. 3, the acquisition function 442 acquires CT image data from the X-ray CT apparatus 100 or the image storage apparatus 300 (Step S101). The CT image data is volume data acquired for a region including the heart of the subject P.

Thereafter, the acquisition function 442 acquires an oval fossa region R1 corresponding to the oval fossa, and a target region R2 corresponding to the treatment target region from the CT image data indicating the heart of the subject P (Step S102). The treatment target region is a region serving as a target of the operation. For example, in the treatment of mitral insufficiency, the treatment target region is a part to be clipped with the clip in the mitral valve. The medical device is required to reach the treatment target region, as a prerequisite for the execution of the operation.

For example, the acquisition function 442 acquires the oval fossa region R1 from the CT image data by segmentation. As an example, the acquisition function 442 performs segmentation using region growing extracting a region in which CT values are spatially continuous and/or pattern matching using a shape template to specify a region corresponding to the oval fossa region in the CT image data. The acquisition function 442 acquires the specified region as the oval fossa region R1.

Figure 4:
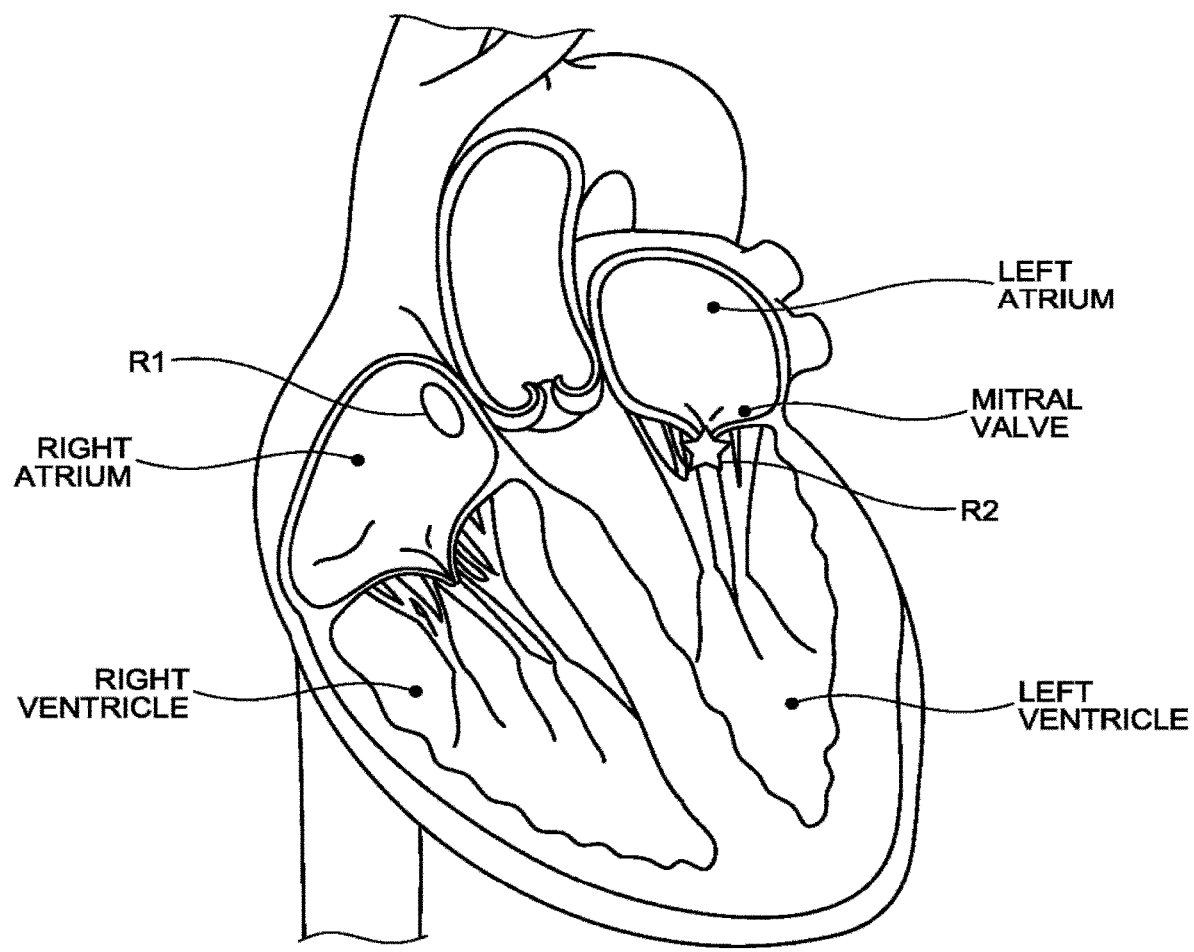
FIG. 4 is a diagram for explaining acquisition of a target region according to the first embodiment.

In addition, for example, the acquisition function 442 acquires the target region R2 from the CT image data, on the basis of an operation by the operator. The following is an explanation of an example of acquisition of the target region R2 with reference to FIG. 4. FIG. 4 is a diagram for explaining an example of acquisition of the target region R2 according to the first embodiment. First, the presentation function 444 generates a display image based on CT image data. For example, the presentation function 444 performs rendering by multi planar reconstruction (MPR) on CT image data to generate an MPR image. In addition, for example, the presentation function 444 performs volume rendering (VR) on the CT image data to generate a rendering image.

The presentation function 444 may generate a display image in accordance with the details of the operation. For example, when the operation is made for the purpose of treatment of mitral insufficiency, the acquisition function 442 specifies the region corresponding to the mitral valve in CT image data using segmentation. The presentation function 444 generates a MPR image or a rendering image to include the region corresponding to the mitral valve.

Thereafter, the presentation function 444 displays the CT image on the display 420. For example, as illustrated in FIG. 4, the presentation function 444 displays a rendering image on the display 420. The rendering image illustrated in FIG. 4 is an image of the heart sectioned with a cross section including the mitral valve, the right atrium, the right ventricle, the left atrium, and the left ventricle, as viewed from the cross-section side. The acquisition function 442 receives designation of the treatment target region from the operator to acquire the target region R2. For example, the operator determines a part suitable for clipping with the clip in the mitral valve, with reference to the rendering image, and designates the determined part through the input interface 410. The acquisition function 442 acquires the designated part as the target region R2. The acquisition function 442 may acquire the target region R2 as a point, or as a region having a certain area or volume. The following explanation illustrates the case where the acquisition function 442 acquires the target region R2 as a point, as an example.

Figure 5:
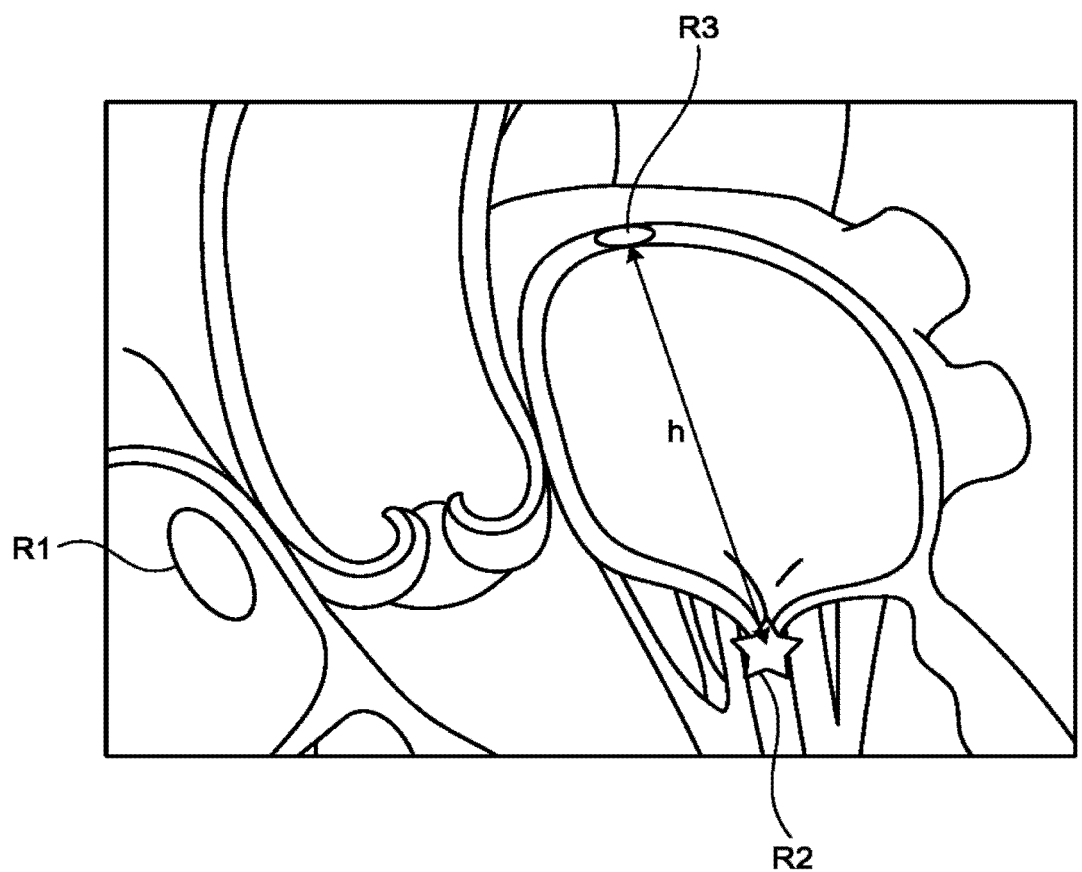
FIG. 5 is a diagram for explaining height from the target region to a region corresponding to an upper part of the left atrium according to the first embodiment.

As illustrated in FIG. 3, after the acquisition function 442 acquires the oval fossa region R1 and the target region R2, the calculation function 443 calculates height "h" from the target region R2 to a region R3 corresponding to the upper part of the left atrium (Step S103). For example, first, as illustrated in FIG. 5, the calculation function 443 specifies a region having the largest distance from the target region R2, as the region R3, in the region corresponding to the left atrium in CT image data. FIG. 5 is a diagram for explaining the height "h" from the target region R2 to the region R3 corresponding to the upper part of the left atrium according to the first embodiment. The calculation function 443 may acquire the region R3 as a point, or as a region having a certain area or volume. The following description illustrates the case where the calculation function 443 acquires the region R3 as a point, as an example. As illustrated in FIG. 5, the calculation function 443 calculates the height "h" from the target region R2 to the region R3.

The region R3 illustrated in FIG. 5 is an example, and the calculation function 443 may specify a region different from that in FIG. 5 as the region R3 corresponding to the upper part of the left atrium. For example, the calculation function 443 may specify a region located in the body axis direction of the subject P from the target region R2, as the region R3, in the region corresponding to the left atrium in the CT image data, and calculate the height "h" from the target region R2 to the region R3.

Thereafter, the calculation function 443 adjusts the puncturing region in the oval fossa region R1, on the basis of the height "h" (Step S104). The puncturing region is a region on the oval fossa region R1 to enable the medical device to reach the treatment target region.

For example, the calculation function 443 adjusts the puncturing region such that the medical device is enabled to reach the treatment target region without coming into contact with the contact-prohibited region. The contact-prohibited region is set to at least a part of the heart. For example, the contact-prohibited region is an internal wall in the ventricle in the heart of the subject P, an internal wall in the atrium, and various valves. For example, in treatment of mitral insufficiency, because it is inevitable that the medical device contacts the mitral valve, the internal wall in the ventricle, the internal wall in the atrium, and the valves other than the mitral valve are set as the contact-prohibited region.

The following description illustrates the case where the internal wall of the left atrium is set as the contact-prohibited region, as an example. In this case, when the puncturing region is punctured, the medical device can reach the treatment target region without coming into contact with the internal wall of the left atrium. The calculating function 443 may calculate the puncturing region by one step from the oval fossa region R1, or calculate the puncturing region by adjusting the puncturing region in a stepped manner from the oval fossa region R1. FIG. 3 illustrates the case where the puncturing region is calculated by adjusting the puncturing region in a stepped manner, at Step S104 and Step S106.

Figure 6A:
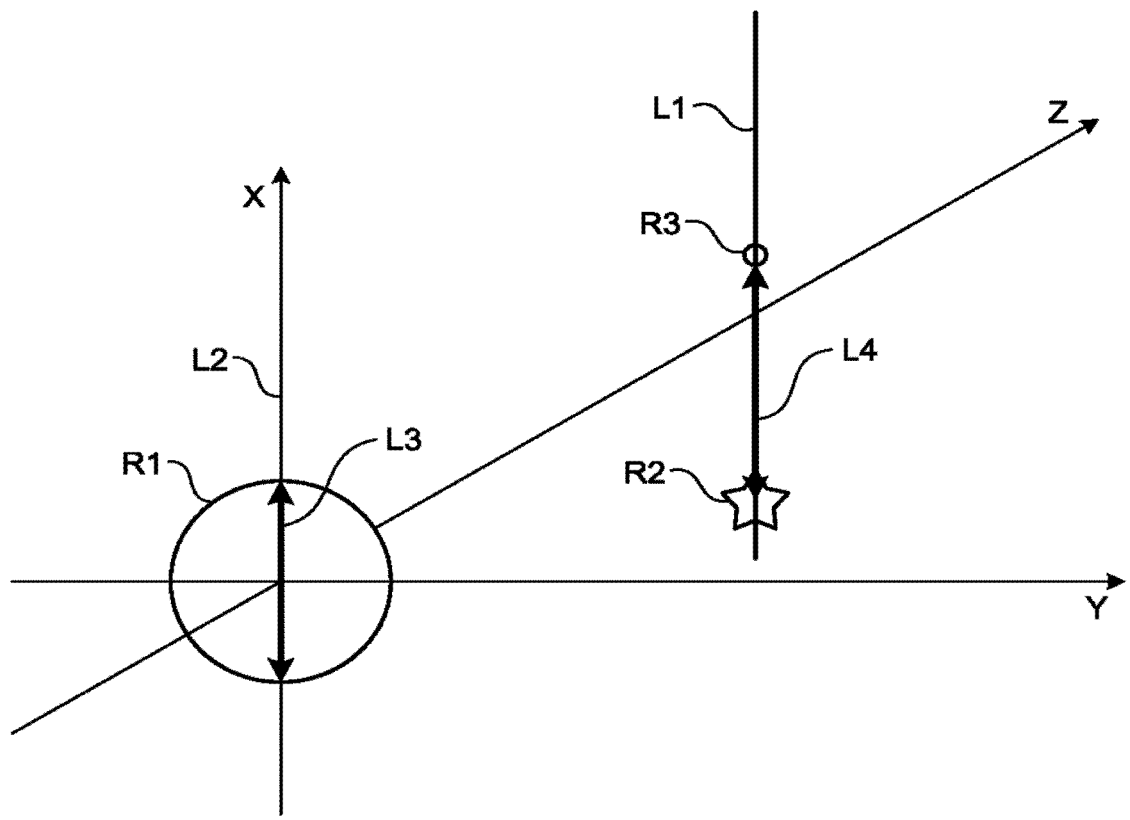
FIG. 6A is a diagram for explaining adjustment of a puncturing region according to the first embodiment.
Figure 6B:
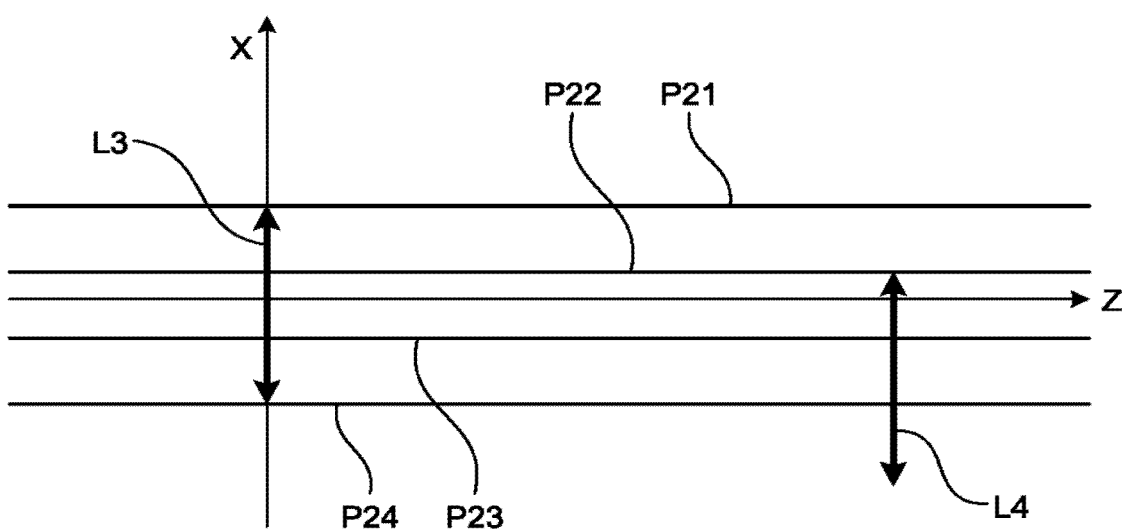
FIG. 6B is a diagram for explaining adjustment of a puncturing region according to the first embodiment.

The following is an explanation of an example of adjustment of the puncturing region at Step S104, with reference to FIG. 6A and FIG. 6B. FIG. 6A and FIG. 6B are diagrams for explaining adjustment of the puncturing region according to the first embodiment. FIG. 6A and FIG. 6B illustrate a rectangular coordinate system, with the center of the oval fossa region R1 serving as the origin. First, the calculation function 443 acquires a plane P1 including the oval fossa region R1, with the oval fossa region R1 regarded as a plane. For example, as illustrated in FIG. 6A, the calculation function 443 regards the oval fossa region R1 as a circular region on an XY plane, and acquires an XY plane including the oval fossa region R1, as the plane P1.

In addition, as illustrated in FIG. 6A, the calculation function 443 acquires a straight line L1 running through the target region R2 and the region R3. FIG. 6A illustrates the case where the straight line L1 is parallel with the X axis and crosses the Z axis, but actually there are cases where the straight line L1 is not parallel with the X axis and does not cross the Z axis.

Thereafter, the calculation function 443 acquires a straight line located on the plane P1 (XY plane) and crossing the straight line L1 or parallel with the straight line L1, as a straight line L2, among straight lines running through the center of the oval fossa region R1. For example, as illustrated in FIG. 6A, when the plane P1 (XY plane) is parallel with the straight line L1, the calculation function 443 acquires a straight line (straight line on the X axis) parallel with the straight line L1, as the straight line L2. By contrast, when the plane 21 (XY plane) is not parallel with the straight line L1, the calculation function 443 acquires a straight line crossing the straight line L1, as the straight line L2, among straight lines on the plane P1 (XY plane) running through the oval fossa region R1. For example, when the straight line L1 is not parallel with the plane P1 (XY plane), the calculation function 443 acquires, as the straight line L2, a straight line running through a point at which the straight line L1 and the XY plane cross and the center of the oval fossa region R1.

Thereafter, as illustrated in FIG. 6A, the calculation function 443 acquires a line segment L3 included in the oval fossa region R1, in the straight line L2. The calculation function 443 also acquires a line segment L4 corresponding to the height "h" in the straight line L1, as illustrated in FIG. 6A. Specifically, the line segment L4 is a line segment extending between the target region R2 and the region R3. The calculation function 443 also acquires a plane P2 perpendicular to the line segment L3, for each of positions on the line segment L3. For example, as illustrated in FIG. 6B, the calculation function 443 acquires a plane P21, a plane P22, a plane P23, and a plane P24 being XY planes, for respective positions on the line segment L3. The plane P2 serves as innumerable planes generated for respective positions on the line segment L3. However, for the sake of convenience of explanation, FIG. 6B illustrates only four planes, that is, the plane P21, the plane P22, the plane P23, and the plane P24, as examples of the plane P2.

The calculation function 443 performs adjustment such that a region in the oval fossa region R1 included in a set of planes P2 crossing the line segment L4 is set as the puncturing region. For example, in FIG. 6B, because the plane P21 does not cross the line segment L4, the calculation function 443 performs adjustment such that the region included in the plane P21 in the oval fossa region R1 is excluded from the puncturing region. By contrast, in FIG. 6B, because the planes P22, P23, and P24 cross the line segment L4, the calculation function 443 performs adjustment such that the region included in the planes P22, P23, and P24 in the oval fossa region R1 is included in the puncturing region.

By puncturing through the puncturing region adjusted at Step S104, the medical device can avoid contact with the left atrium. In other words, the calculation function 443 determines at Step S104 whether the medical device contacts the internal wall of the left atrium, on the basis of the height "h", to calculate a puncturing region enabling the medical device to avoid contact with the internal wall of the left atrium.

The following is a specific explanation of the puncturing region adjusted at Step S104. First, because puncture becomes easier as the needle becomes more perpendicular to the oval fossa, the needle punctures the oval fossa substantially perpendicularly in many cases. After the needle punctures the oval fossa, the guide wire substantially straightly advances through the inside of the left atrium, at an angle substantially equal to the angle at which the needle has punctured the oval fossa (that is, substantially perpendicularly to the oval fossa), by a sufficient length to introduce the catheter into the left atrium. In this state, when the puncturing region adjusted at Step S104 has been punctured, the guide wire reaches a region between the treatment target region and the upper part of the left atrium, without coming into contact with the internal wall of the left atrium. By contrast, when a region other than the puncturing region adjusted at Step S104 has been punctured, the guide wire may come into contact with the internal wall of the upper part or the lower part of the left atrium, when it runs through the oval fossa and substantially straightly advances through the inside of the left atrium. Accordingly, by puncturing through the puncturing region adjusted at Step S104, the medical device can avoid contact with the left atrium.

At Step S104, the calculation function 443 may adjust the puncturing region, also in consideration of the behavior of the medical device in the left atrium. For example, the calculation function 443 may adjust the puncturing region using device information relating to the movable range of the medical device. Specifically, in some movable ranges of the medical device and some puncturing position in the oval fossa, there are cases where the medical device cannot reach the treatment target region, although the medical device reaches the inside of the left atrium. For example, because the bending angle of the medical device is restricted (such as the number of bendable joints and the maximum value of the bending angle of each of the joints), in some puncturing positions of the oval fossa, there are cases where the medical device cannot reach the treatment target region, although the medical device reaches the inside of the left atrium. For this reason, the calculation function 443 adjusts the puncturing region such that the medical device that has punctured through the oval fossa is enabled to reach the treatment target region, on the basis of the restriction relating to the bending angle of the medical device.

For example, first, the acquisition function 442 acquires the restriction relating to the bending angle for the medical device used for the operation. For example, the acquisition function 442 receives an input operation from the operator through the input interface 410, to acquire information, such as the positions and the number of bendable joints in the medical device, the maximum value of the angle at which each of the joints is bent, the bending direction, and the curvature in bending. The acquisition function 442 also acquires positional relation between the oval fossa region R1 and the target region R2. Thereafter, the calculation function 443 determines whether the medical device can reach the target region R2, for each of positions in the oval fossa region R1, in the case where the medical device is advanced with the position serving as the starting point and bent under the restriction relating to the bending angle. The calculation function 443 calculates a set of positions determined as positions with which the medical device can reach the target region R2, in the oval fossa region R1, as puncturing regions enabling the medical device to reach the treatment target region.

Figure 7A:
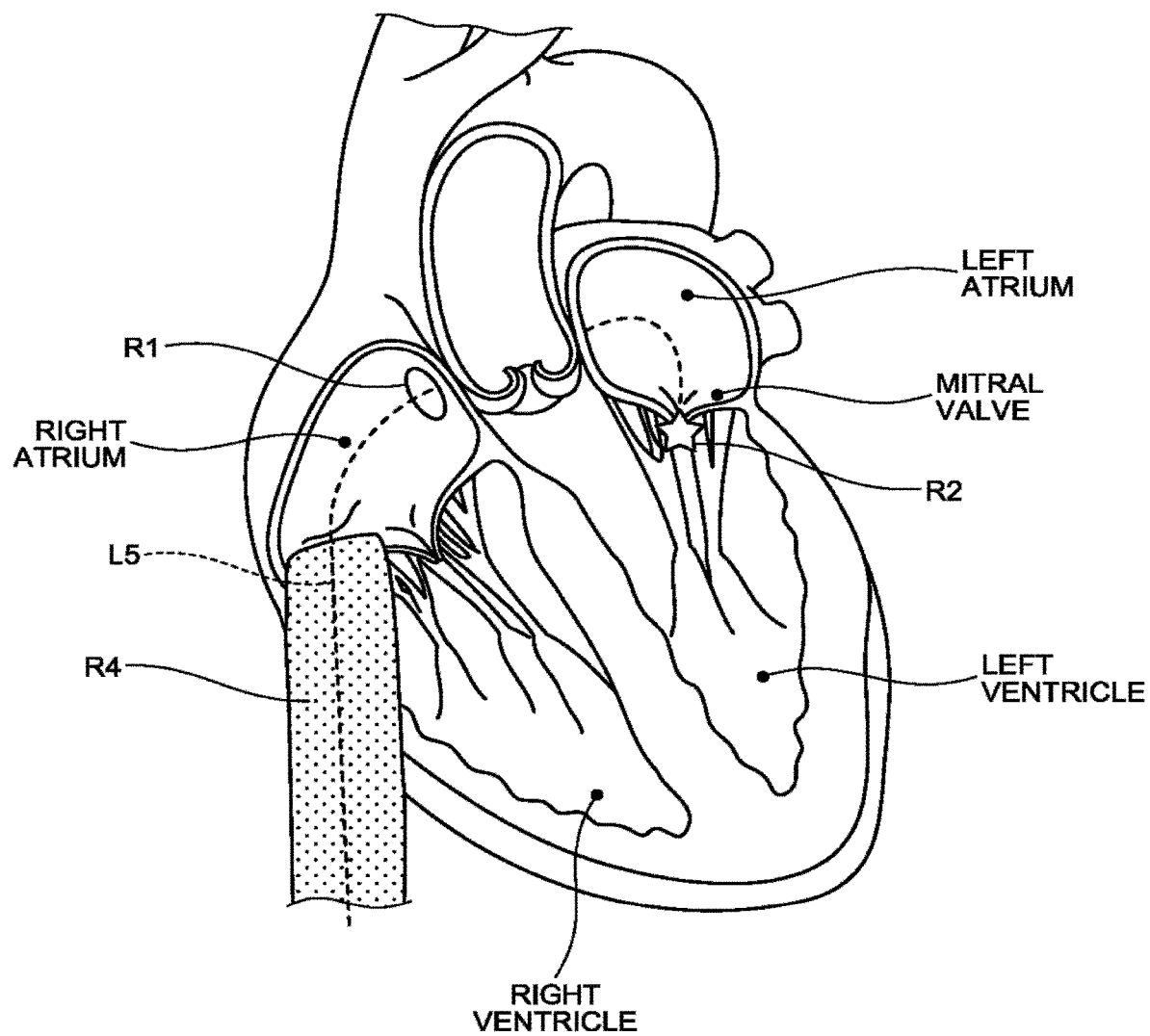
FIG. 7A is a diagram for explaining a line connecting the target region with an inferior vena cava region according to the first embodiment.

Thereafter, the calculation function 443 generates a line L5 connecting the target region R2 with the inferior vena cava region R4 (Step S105). For example, first, the acquisition function 442 acquires the inferior vena cava region R4 corresponding to the inferior vena cava from the CT image data. The inferior vena cava region R4 does not correspond to the whole inferior vena cava of the subject P, but may correspond to part of the inferior vena cava. For example, as illustrated in FIG. 7A, the acquisition function 442 acquires the inferior vena cava region R4 corresponding to a part of the inferior vena cava located in the vicinity of the heart. FIG. 7A is a diagram for explaining the line L5 connecting the target region R2 with the inferior vena cava region R4 according to the first embodiment.

Figure 7B:
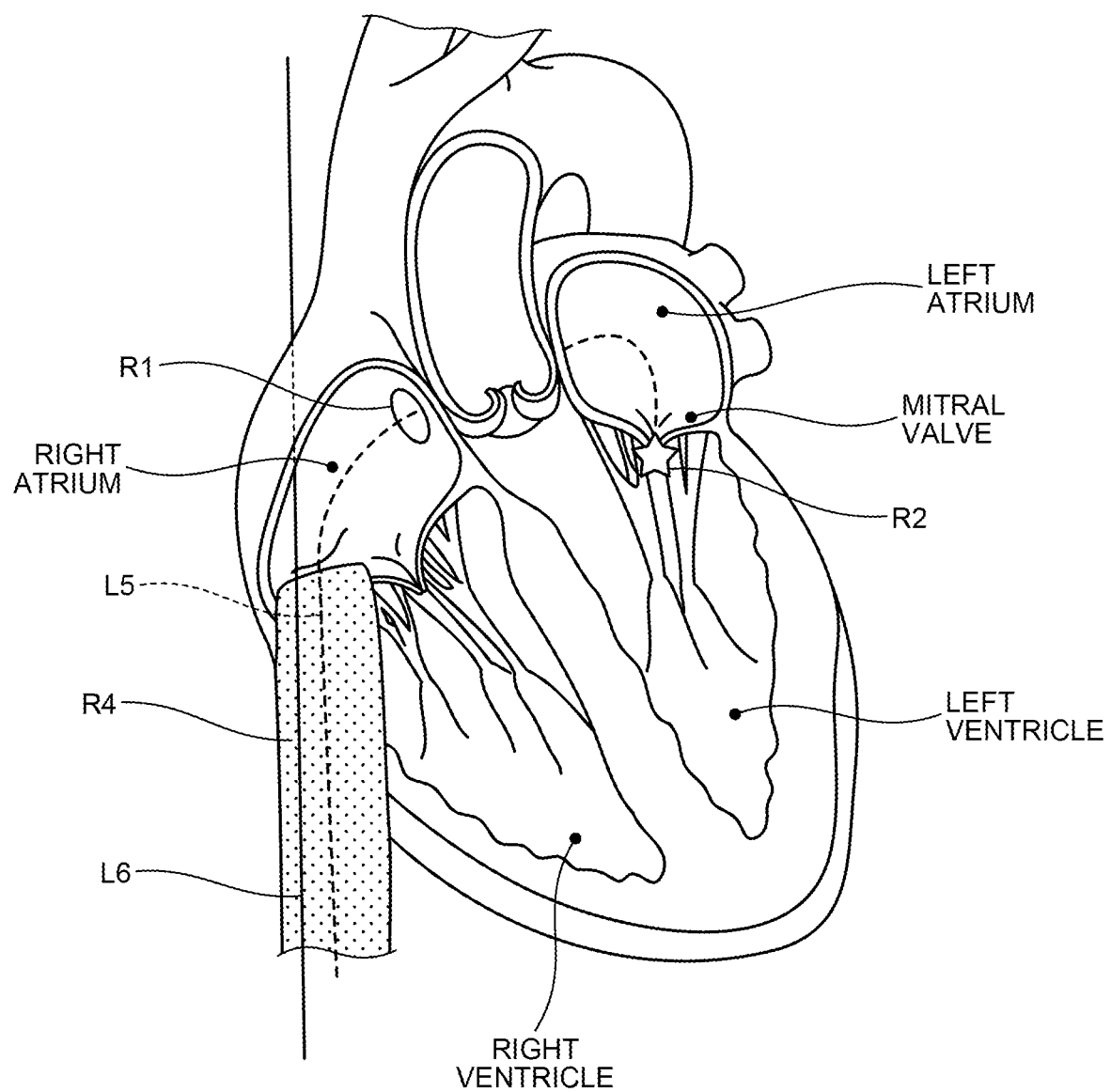
FIG. 7B is a diagram for explaining a line connecting the target region with an inferior vena cava region according to the first embodiment.
Figure 7C:
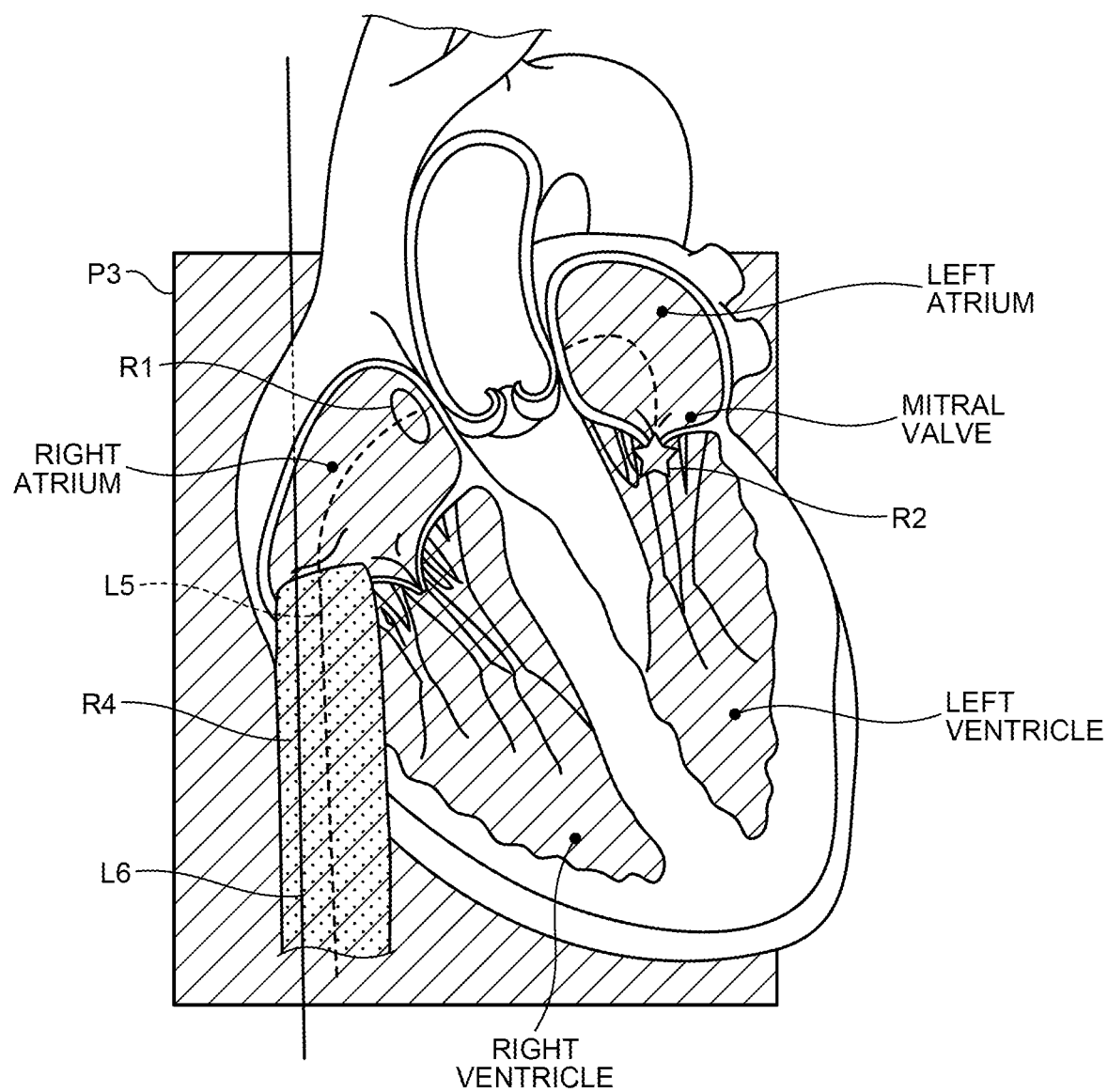
FIG. 7C is a diagram for explaining a line connecting the target region with an inferior vena cava region according to the first embodiment.

Thereafter, as illustrated in FIG. 7A, the calculation function 443 generates the line L5 such that the line L5 runs through the inferior vena cava region R4, the puncturing region (puncturing region adjusted at Step S104) in the oval fossa region R1, and the target region R2. For example, first, the calculation function 443 extracts a core line in the inferior vena cava region R4, as a straight line. Thereafter, the calculation function 443 acquires a plurality of straight lines L6 parallel with the extracted core line and running through the inferior vena cava region R4. FIG. 7B illustrates lines L6. Lines L6 are illustrated as a straight line in FIG. 7B. However, the lines L6 are a plurality of straight lines meeting above definition. The calculation function 443 generates a plurality of lines L5 for each of the straight lines L6, as two-dimensional curves on the plane P3 including the straight line L6 and the target region R2. FIG. 7C illustrates the plane P3. The plane P3 is illustrated as a plane in FIG. 7C. However, the plane P3 is a plurality of planes defined for each of the lines L6.

Figure 7D:
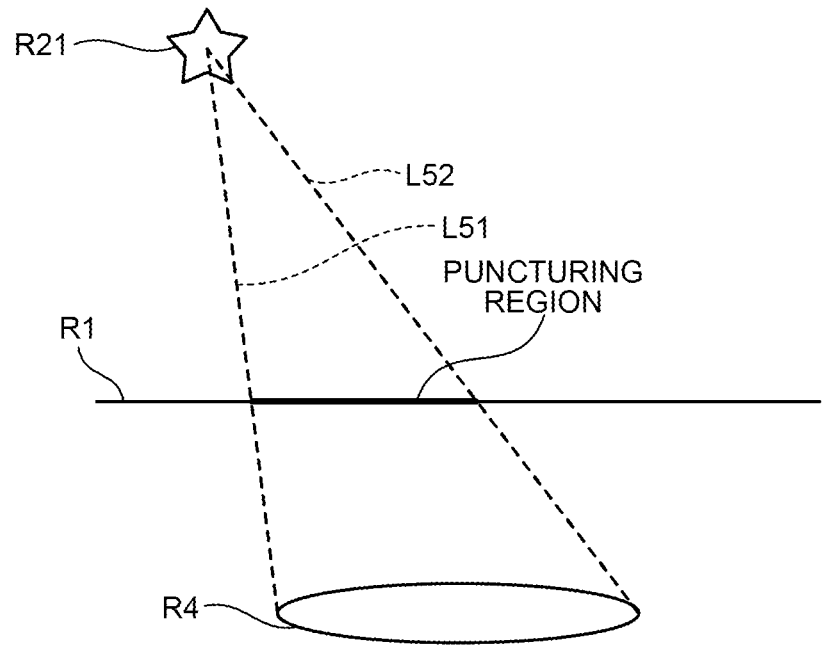
FIG. 7D is a diagram for explaining a line connecting the target region with the inferior vena cava region according to the first embodiment.

The following is a more detailed explanation of the line L5 with reference to FIG. 7D. FIG. 7D is a diagram for explaining the line L5 connecting the target region R2 with the inferior vena cava region R4 according to the first embodiment. FIG. 7D corresponds to a diagram illustrating the inferior vena cava region R4, the oval fossa region R1, the target region R2, and the line L5 in FIG. 7A, as viewed from the core line direction of the inferior vena cava region R4. For example, the left side in FIG. 7D corresponds to the back side of the subject P, and the right side corresponds to the abdomen side of the subject P. FIG. 7D illustrates the target region R21 as an example of the target region R2. The target region R21 is a point designated by the operator as a position suitable to be clipped with the clip in the mitral valve.

Figure 7E:
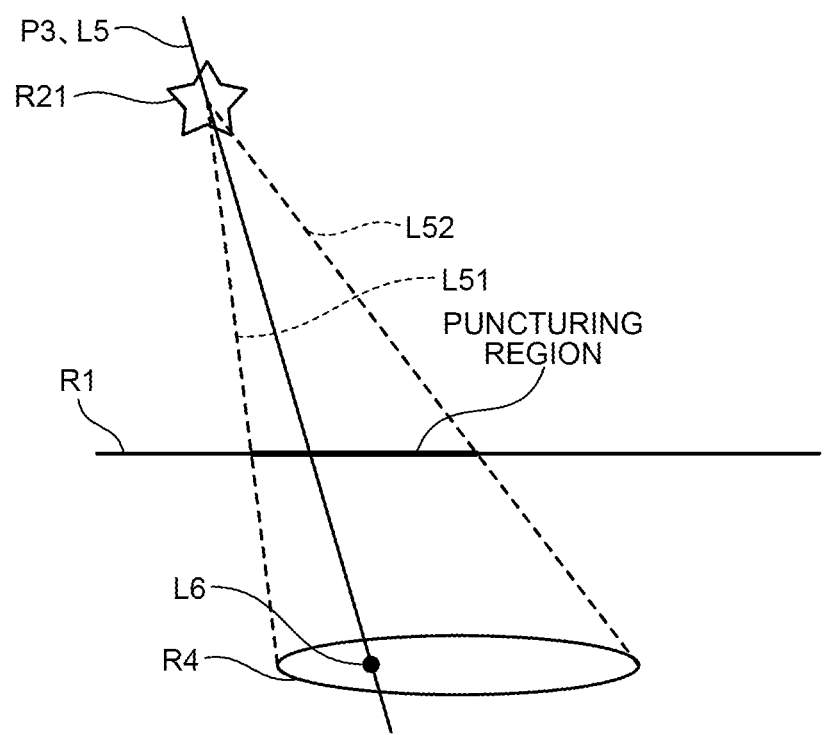
FIG. 7E is a diagram for explaining a line connecting the target region with an inferior vena cava region according to the first embodiment.

First, the calculation function 443 extracts the core line in the inferior vena cava region R4 as a straight line, and acquires a plurality of straight lines L6 parallel with the extracted core line and running through the inferior vena cava region R4. In FIG. 7D, each of the straight lines L6 serves as a point in the inferior vena cava region R4. For example, one of the straight lines L6 is illustrated as a point in the inferior vena cava region R4 as in FIG. 7E. Thereafter, the calculation function 443 acquires a plurality of planes P3 including the straight lines L6 and the target region R21, for the respective straight lines L6. As shown in FIG. 7E, each of the planes P3 serves as a straight line running through the inferior vena cava region R4 and the target region R21. Each of the lines L5 serving as a two-dimensional curve on the respective planes P3 also serves as a straight line running through the inferior vena cava region R4 and the target region R21, as in FIG. 7E.

In FIG. 7D, the lines L5 are innumerable lines generated for the respective positions of the inferior vena cava region R4. For the sake of convenience of explanation, FIG. 7D illustrates a line L51 and a line L52, as examples of the line L5. The line L51 is a line miming through the position closest to the back side of the subject P in the inferior vena cava region R4 and the target region R21. The line L52 is a line running through the position closest to the abdomen side of the subject P in the inferior vena cava region R4 and the target region R21.

Thereafter, the calculation function 443 adjusts the puncturing region in the oval fossa region R1, on the basis of the lines L5 (Step S106). For example, as illustrated in FIG. 7D, the calculation function 443 calculates respective intersection points between the oval fossa region R1 and the line L51 and the line L52, and performs adjustment to set a part located between the calculated intersection points as the puncturing region.

By puncturing the puncturing region adjusted at Step S106, the medical device can reach the treatment target region. In other words, at Step S106, the calculation function 443 determines whether the medical device can reach the treatment target region, on the basis of the lines L5, to calculate the puncturing region enabling the medical device to reach the treatment target region.

The following is a specific explanation of the puncturing region adjusted at Step S106. First, after the medical device reaches the right atrium through the inferior vena cava, the medical device is bent toward the puncturing region of the oval fossa to puncture the oval fossa. In addition, even after the medical device has punctured the oval fossa, a part of the medical device located in the inferior vena cava is movable in the inferior vena cava. Accordingly, the medical device that has punctured the oval fossa is further bendable at least on the plane including the inferior vena cava and the puncturing region. When the treatment target region is located on such a plane, the medical device can reach the treatment target region by being bent, in many cases. When the medical device has punctured the puncturing region illustrated in FIG. 7B, the treatment target region is located on the plane including the inferior vena cava and the puncturing region, and the medical device can reach the treatment target region.

By contrast, the medical device is not always bendable in a direction (direction going away from the plane) that is not parallel with the plane including the inferior vena cava and the puncturing region. For this reason, when the medical device punctures a position other than the puncturing region illustrated in FIG. 7B and the treatment target region is not located on the plane including the inferior vena cava and the puncturing region, there are cases where the medical device cannot reach the treatment target region, due to restrictions on the bending direction of the medical device.

The puncturing region illustrated in FIG. 7B is a region included in innumerable planes P3 including the lines L5 serving as curves in the oval fossa region R1, in a three-dimensional manner. When the processing at Step S105 and Step S106 is expressed in other words in a three-dimensional manner, the calculation function 443 determines whether the medical device can reach the treatment target region when the medical device punctures each of the positions in the oval fossa region R1, according to whether each of the positions in the oval fossa region R1 is included in the plane P3, to calculate the puncturing region.

FIG. 7D illustrates the target region R21 as an example of the target region R2 corresponding to the target treatment region, but a plurality of target regions R2 may exist. For example, in an operation of clipping a plurality of positions in the mitral valve with clips, the acquisition function 442 may acquire each of a plurality of positions at which the clips are left, as the target regions R2.

Figure 7F:
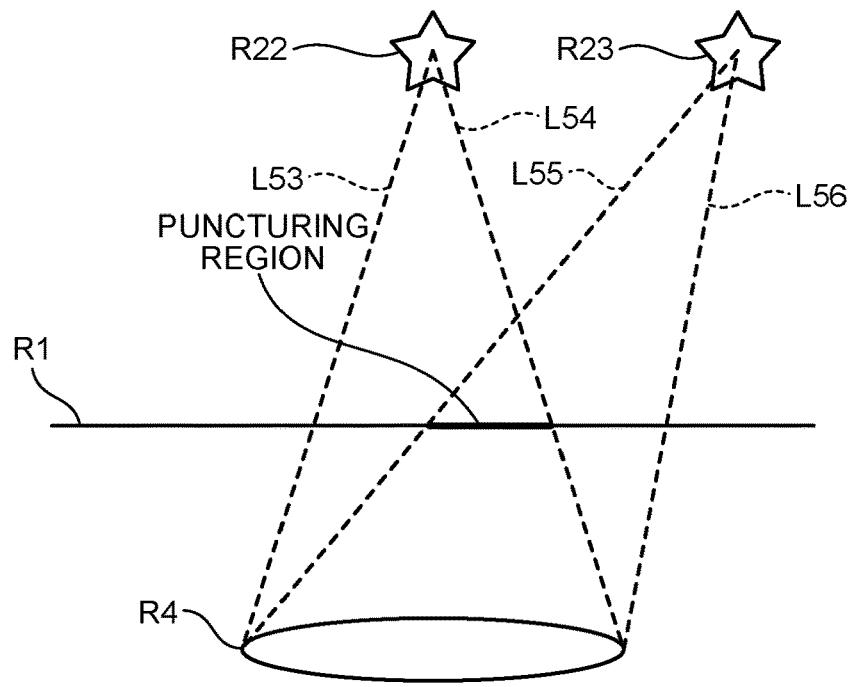
FIG. 7F is a diagram for explaining lines connecting the target regions with the inferior vena cava region according to the first embodiment.

The following is an explanation of the case where a plurality of target regions R2 exist, with reference to FIG. 7F. FIG. 7F is a diagram for explaining lines L5 connecting the target regions R2 with the inferior vena cava region R4 according to the first embodiment. FIG. 7F corresponds to a diagram illustrating the inferior vena cava region R4, the oval fossa region R1, the target regions R2, and the lines L5 in FIG. 7A, as viewed from the core line direction of the inferior vena cava region R4, in the same manner as FIG. 7D. For example, the left side in FIG. 7F corresponds to the back side of the subject P, and the right side corresponds to the abdomen side of the subject P. FIG. 7F illustrates the target region R22 and the target region R23 as examples of the target region R2. The target region R22 and the target region R23 are a plurality of points designated by the operator as positions suitable to be clipped with the clips in the mitral valve.

Figure 7G:
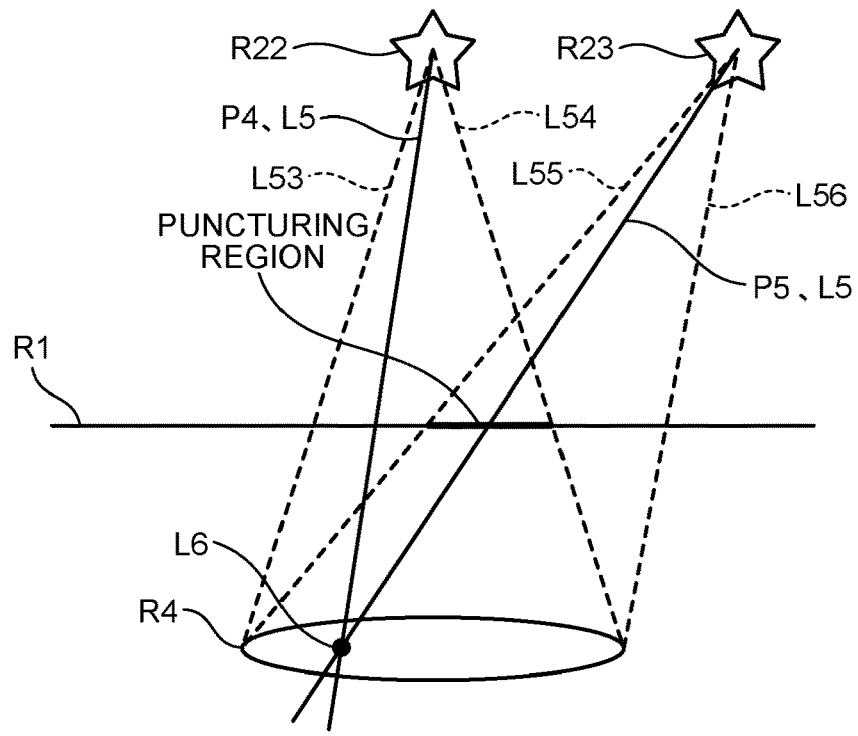
FIG. 7G is a diagram for explaining a line connecting the target region with an inferior vena cava region according to the first embodiment.

First, the calculation function 443 extracts the core line in the inferior vena cava region R4 as a straight line, and acquires a plurality of straight lines L6 parallel with the extracted core line and running through the inferior vena cava region R4. In FIG. 7F, each of the straight lines L6 serves as innumerable points in the inferior vena cava region R4. For example, one of the straight lines L6 is illustrated as a point in the inferior vena cava region R4 as in FIG. 7G. Thereafter, the calculation function 443 acquires a plurality of planes P4 including the straight lines L6 and the target region R22, and a plurality of planes P5 including the straight lines L6 and the target region R23 for the respective straight lines L6. As shown in FIG. 7G, each of the planes P4 serves as a straight line running through the inferior vena cava region R4 and the target region R22, and each of the planes P5 serves as a straight line running through the inferior vena cava region R4 and the target region R23.

The calculation function 443 generates lines L5 running through the inferior vena cava region R4, the oval fossa region R1, and the target region R22 or the target region R23, as two-dimensional curves on the plane P4 or the plane P5. In FIG. 7F, each of the lines L5 is a straight line running through the inferior vena cava region R4, the oval fossa region R1, and the target region R22 or the target region R23. In FIG. 7F, the lines L5 are innumerable lines generated for the respective positions of the inferior vena cava region R4.

For the sake of convenience of explanation, FIG. 7F illustrates only lines L53 and L54, as examples of the line L5 running through the target region R22. The line L53 is a line running through the position closest to the back side of the subject P in the inferior vena cava region R4 and the target region R22. The line L54 is a line running through the position closest to the abdomen side of the subject P in the inferior vena cava region R4 and the target region R22. In addition, FIG. 7F illustrates only lines L55 and L56, as examples of the line L5 running through the target region R23. The line L55 is a line running through the position closest to the back side of the subject P in the inferior vena cava region R4 and the target region R23. The line L56 is a line running through the position closest to the abdomen side of the subject P in the inferior vena cava region R4 and the target region R23.

Thereafter, the calculation function 443 adjusts the puncturing region in the oval fossa region R1, on the basis of the lines L5. For example, the calculation function 443 calculates respective intersection points between the oval fossa region R1 and the line L53, the line L54, the line L55, and the line L56, in the oval fossa region R1. The calculation function 443 performs adjustment to set a region at which a region located between the intersection points of the line L53 and the line L54 overlaps a region located between the intersection points of the line L55 and the line L56, as the puncturing region. By puncturing the puncturing region adjusted as described above, the medical device can reach a plurality of treatment target regions by puncturing one location of the oval fossa.

Specifically, first, the medical device including the first clip punctures the puncturing region illustrated in FIG. 7F. For example, the medical device punctures the puncturing position illustrated in FIG. 7H, in the puncturing region.

Figure 7H:
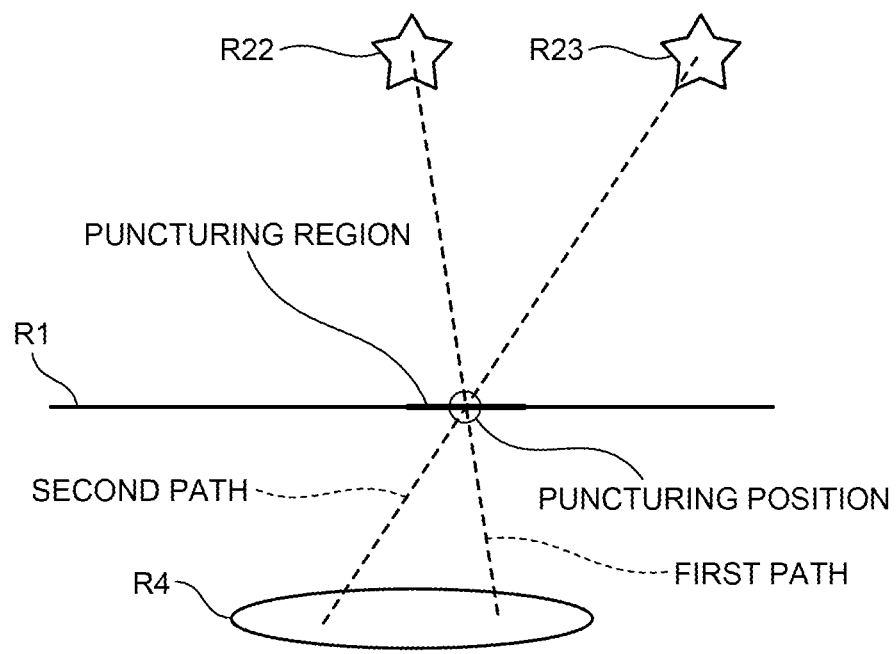
FIG. 7H is a diagram for explaining paths of the medical device in the case where a plurality of treatment target regions exist according to the first embodiment.

FIG. 7H is a diagram for explaining paths of the medical device in the case where a plurality of treatment target regions exist according to the first embodiment. The first path illustrated in FIG. 7H is a two-dimensional curve on a plane extending through the inferior vena cava region R4, the puncturing position, and the target region R22, in a three-dimensional manner. The second path illustrated in FIG. 7H is a two-dimensional curve on a plane extending through the inferior vena cava region R4, the puncturing position, and the target region R23, in a three-dimensional manner.

The medical device including the first clip reaches the inside of the left atrium through the puncturing position in FIG. 7H, according to the first path, and is bent in the left atrium to reach the target region R22. Thereafter, the medical device indwells the first clip in the target region R22, and thereafter is extracted out of the subject P. Thereafter, the medical device including the second clip reaches the inside of the left atrium through the puncturing position in FIG. 7H, according to the second path, and is bent in the left atrium to reach the target region R23. Thereafter, the medical device indwells the second clip in the target region R23, and thereafter is extracted out of the subject P. Specifically, by puncturing the puncturing region illustrated in FIG. 7F and FIG. 7H, the puncturing position in the oval fossa is limited to one location also in the operation indwelling a plurality of clips, and the burden on the subject P is reduced.

The flowchart of FIG. 3 illustrates the case of calculating the puncturing region on the basis of the height "h" and the line L5, but the embodiment is not limited thereto. For example, the calculation function 443 may calculate the puncturing region in consideration of the aorta in the heart of the subject P. As an example, first, the acquisition function 442 performs blood vessel extraction processing on the CT image data to acquire an aortic region corresponding to the aorta. Thereafter, the calculation function 443 calculates a region having a distance equal to or larger than a threshold T1 from the aortic region, in the oval fossa region R1. The threshold T1 may be a preset fixed value, or a value set by the operator or the like. The calculation function 443 calculates the puncturing region on the basis of the height "h" and the lines L5, in the region having a distance equal to or larger than the threshold T1 from the aortic region, in the oval fossa region R1. This structure prevents the medical device from coming into contact with the aorta of the subject P while the medical device punctures the oval fossa.

In addition, the presentation function 444 may present a region having a distance equal to or smaller than a threshold T2 from the aortic region. For example, the presentation function 444 presents a region having a distance equal to or smaller than the threshold T2 from the aortic region, in the oval fossa region R1, in the CT image and/or the ultrasonic image. Specifically, the presentation function 444 presents a location (such as a warning mark) that is not to be punctured, for the part close to the aorta. This structure prevents the medical device from coming into contact with the aorta of the subject P while the medical device punctures the oval fossa. The threshold T2 may be a preset fixed value, or a value set by the operator or the like. The threshold T2 may be the same value as the threshold T1, or a value different from the threshold T1.

In addition, for example, the calculation function 443 may calculate the puncturing region in consideration of the thickness of the oval fossa. As an example, first, the acquisition function 442 acquires thickness for each of positions of the oval fossa region R1 acquired from the CT image data. Thereafter, the calculation function 443 calculates a region having a thickness equal to or smaller than a threshold T3, in the oval fossa region R1. The threshold T3 may be a preset fixed value, or a value set by the operator or the like. The calculation function 443 calculates the puncturing region on the basis of the height "h" and the lines L5, in the region having a thickness equal to or smaller than a threshold T3, in the oval fossa region R1. This structure enables the medical device to avoid a thick part in the oval fossa, and easily puncture a thick part in the oval fossa.

In addition, the presentation function 444 may select a needle on the basis of the thickness of the puncturing region calculated with the calculation function 443 to present the selected needle. For example, first, the presentation function 444 acquires a mean value and/or a maximum value of the thicknesses in the respective positions of the puncturing region, as the thickness of the puncturing region. Thereafter, the presentation function 444 selects a needle on the basis of the acquired thickness of the puncturing region, and displays the selected needle on the display 420. For example, the presentation function 444 displays an image illustrating the selected needle and/or information relating to the shape of the needle on the display 420. The control function 441 may receive an operation to determine whether to use the presented catheter for the operation from the operator.

Figure 8A:
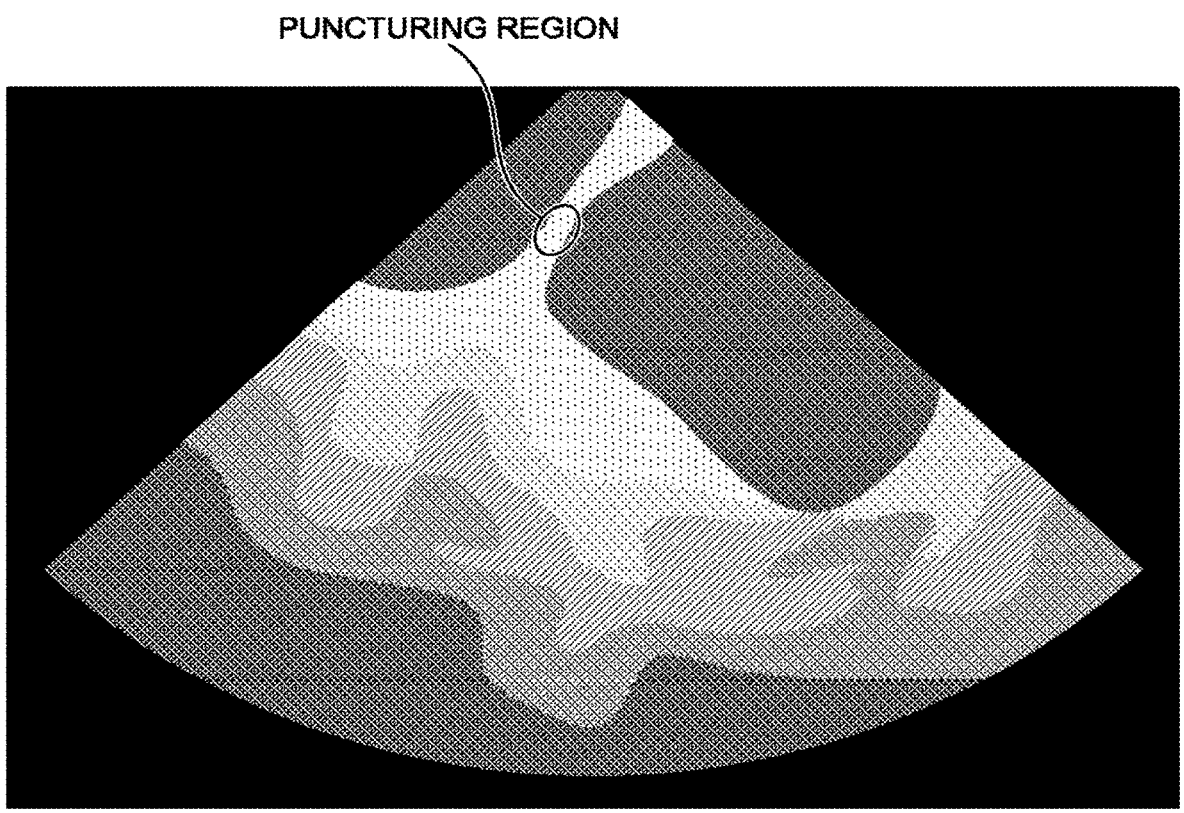
FIG. 8A is a diagram illustrating an example of presenting the puncturing region according to the first embodiment.

After the calculation function 443 calculates the puncturing region, the presentation function 444 presents the puncturing region to the operator (Step S107). For example, the presentation function 444 displays the CT image on the display 420, and displays the puncturing region on the CT image. As another example, as illustrated in FIG. 8A, the presentation function 444 displays the puncturing region on the ultrasonic image imaged with the ultrasonic diagnostic apparatus 200. FIG. 8A is a diagram illustrating an example of presenting the puncturing region according to the first embodiment. The ultrasonic image illustrated in FIG. 8A is an ultrasonic image obtained by actually imaging the region including the heart of the subject P, and a two-dimensional B-mode image in which the intensity of reflective waves is indicated with luminance.

The following is a specific explanation of display of the puncturing region using an ultrasonic image. First, the presentation function 444 performs positioning of the CT image data with the ultrasonic image data to identify the puncturing region in the ultrasonic image data. As an example, in the ultrasonic diagnostic apparatus 200, an ultrasonic probe provided with a sensor acquiring positional information and angle information acquires ultrasonic image data of the subject P, and the same feature points as anatomical feature points drawn on the CT image data are designated on the ultrasonic image data to associate the coordinate system of the ultrasonic image data determined according to the position and the angle of the sensor at the time with the coordinate system of the CT image data. In this manner, the coordinates of the puncturing region calculated in the CT image data are identified in the coordinate system of the ultrasonic image data.

The presentation function 444 provides the coordinates identified as coordinates of the puncturing region with a mark and/or color indicating that the coordinates are the puncturing region, in the ultrasonic image obtained by actually imaging the region including the heart of the subject P to display the coordinates on the display 420. When the medical device has been inserted into the subject P, the presentation function 444 is capable of displaying the puncturing region on the ultrasonic image obtained by imaging the heart of the subject P and the medical device to present the positional relation between the medical device and the puncturing region to the operator.

Figure 8B:
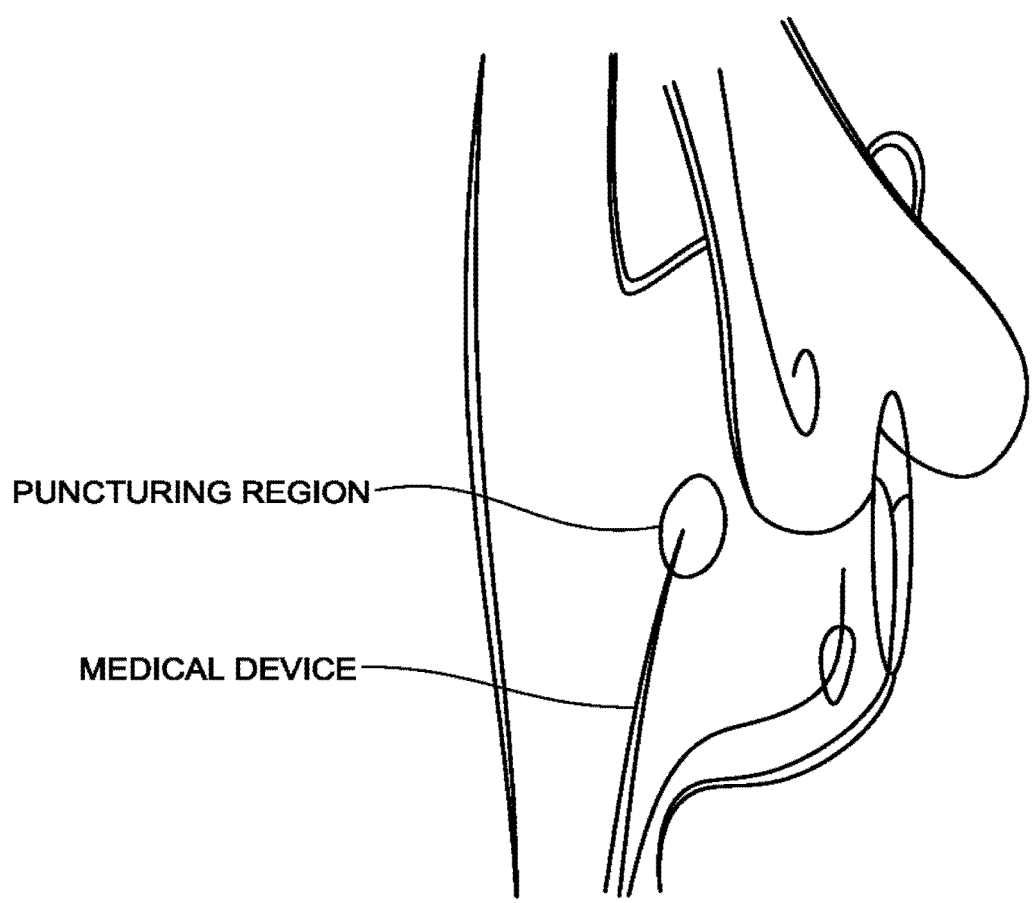
FIG. 8B is a diagram illustrating an example of presenting the puncturing region according to the first embodiment.

The description above has illustrated the case of displaying the puncturing region on an ultrasonic image, but the embodiment is not limited thereto. For example, in the case where the medical image processing system 1 includes an X-ray diagnostic apparatus, the presentation function 444 may display the puncturing region on an X-ray image obtained by actually imaging the region including the heart of the subject P. For example, as illustrated in FIG. 8B, the presentation function 444 displays the puncturing region on an X-ray image obtained by actually imaging the heart of the subject P and the medical device. FIG. 8B is a diagram illustrating an example of presenting the puncturing region according to the first embodiment.

For example, the presentation function 444 performs positioning of the CT image data with the X-ray image data to identify the puncturing region in the X-ray image data and displays the puncturing region on the X-ray image. As an example, first, the X-ray diagnostic apparatus images three-dimensional X-ray image data by rotation imaging. Thereafter, the presentation function 444 performs positioning between the three-dimensional X-ray image data imaged with the X-ray diagnostic apparatus and the CT image data, on the basis of anatomical feature points drawn on each of the image data. In this manner, the presentation function 444 is enabled to identify the puncturing region in the X-ray image data, and display the puncturing region on the X-ray image.

The presentation function 444 may display the path (route) of the medical device, in addition to the puncturing region. For example, the calculation function 443 calculates the path of the medical device to reach the treatment target region through the oval fossa. As an example, the calculation function 443 acquires a region R5 serving as a joining part between the inferior vena cava and the right atrium and is opposed to the puncturing region, from the CT image data. The region R5 is a region serving as the fulcrum of the medical device when the oval fossa is punctured with the needle, and is included in the path of the medical device. The calculation function 443 connects the region R5, the puncturing region, and the target region R2 with a curve, under the restriction relating to the bending angle of the medical device, to calculate the path of the medical device.

Figure 9:
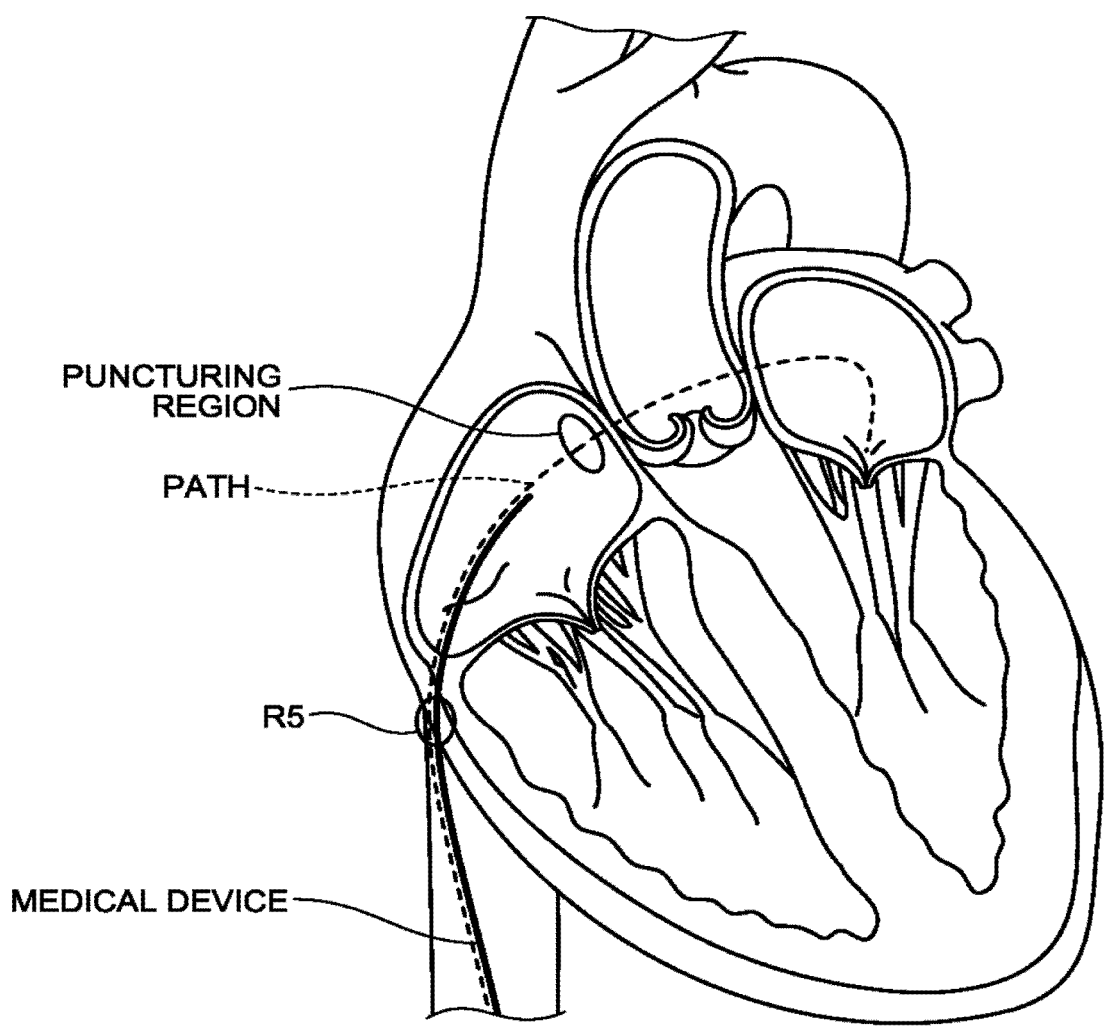
FIG. 9 is a diagram illustrating an example of the puncturing region and the path according to the first embodiment.

For example, the presentation function 444 displays the puncturing region and the path on the CT image data. As an example, as illustrated in FIG. 9, the presentation function 444 displays a CT image on the display 420, and displays the puncturing region and the path on the CT image. The CT image illustrated in FIG. 9 is a rendering image illustrating the heart sectioned with a cross section including the mitral valve, the right atrium, the right ventricle, the left atrium, and the left ventricle, as viewed from the cross-section side. FIG. 9 is a diagram illustrating an example of presenting the puncturing region and the path according to the first embodiment.

The presentation function 444 may display the medical device in addition to the puncturing region and the path. For example, first, the presentation function 444 performs positioning of the CT image data with the ultrasonic image data. As an example, an ultrasonic probe provided with a sensor acquiring positional information and angle information acquires ultrasonic image data of the subject P, and by designating the same feature points on the ultrasonic image data as the anatomical feature points drawn on the CT image data, the coordinate system of the ultrasonic image data determined according to the position and the angle of the sensor at that time are associated with the coordinate system of the CT image data.

Thereafter, the presentation function 444 synthesizes the ultrasonic image data obtained by actually imaging the medical device inserted into the subject P with the CT image data. The ultrasonic image data may be a difference image obtained by removing the background component other than the medical device. For example, the presentation function 444 obtains a difference between the ultrasonic image data after the medical device has been inserted into the subject P and the ultrasonic image data before the medical device is inserted into the subject P, to generate a difference image with the background component removed. As another example, the ultrasonic diagnostic apparatus 200 generates a difference image obtained by removing the background component, and the presentation function 444 acquires the difference image from the ultrasonic diagnostic apparatus 200. As illustrated in FIG. 9, the presentation function 444 displays the CT image, such as a rendering image, on the display 420 on the basis of the CT image data to display the puncturing region, the path, and the real-time medical device on the CT image.

The following is an explanation of another example of display of the medical device. First, in the case where the medical device includes a marker indicating positional information and angle information, the presentation function 444 acquires positional information and angle information of the medical device in the coordinate system of the ultrasonic image data, on the basis of the marker drawn on the ultrasonic image data. Such a marker is formed of, for example, material (such as metal) having acoustic impedance widely different from that of the tissue in the body of the subject P. Thereafter, the presentation function 444 performs positioning of the CT image data with the ultrasonic image data to acquire positional information and angle information of the medical device in the coordinate system of the CT image data. Thereafter, the presentation function 444 displays a CT image based on the CT image data on the display 420, and displays the puncturing region, the path, and the real-time medical device on the CT image. The medical device displayed on the CT image may be an image indicating the medical device drawn on the ultrasonic image data, or a preset image (such as a bar-shaped icon).

The description above illustrates the case of displaying an actually imaged ultrasonic image and the case of displaying a CT image, but the presentation function 444 may display both the ultrasonic image and the CT image. For example, the presentation function 444 performs positioning of the CT image data with the ultrasonic image data, and displays an ultrasonic image displaying the puncturing region and the path, and a CT image displaying the puncturing region and the path side by side.

Figure 10:
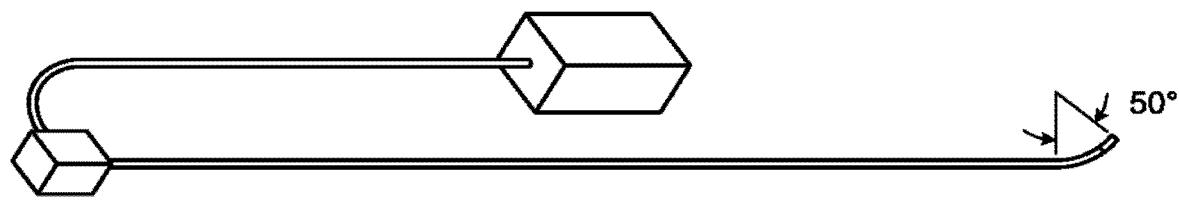
FIG. 10 is a diagram illustrating an example of a catheter according to the first embodiment.
Figure 11A:
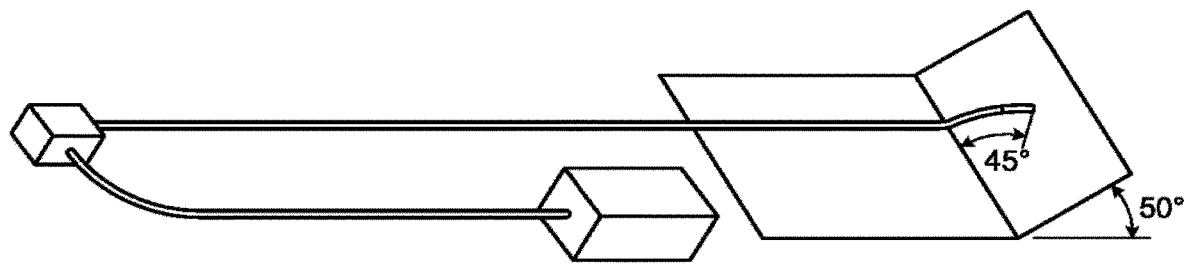
FIG. 11A is a diagram illustrating an example of the catheter according to the first embodiment.
Figure 11B:
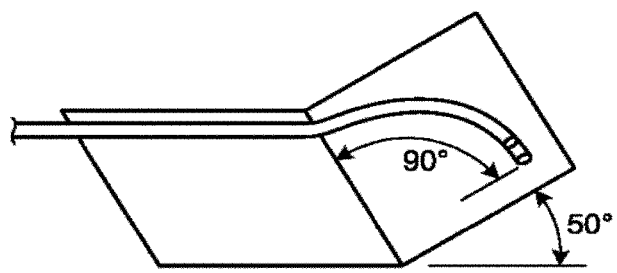
FIG. 11B is a diagram illustrating an example of the catheter according to the first embodiment.
Figure 11C:
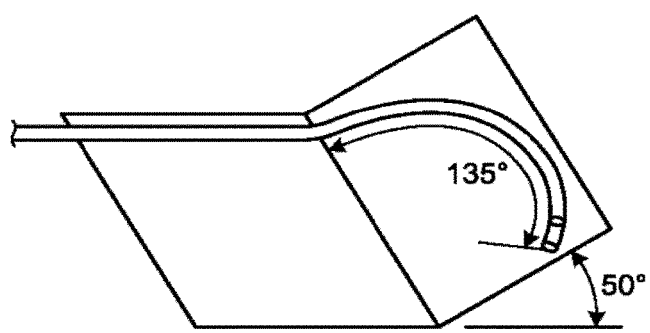
FIG. 11C is a diagram illustrating an example of the catheter according to the first embodiment.
Figure 11D:
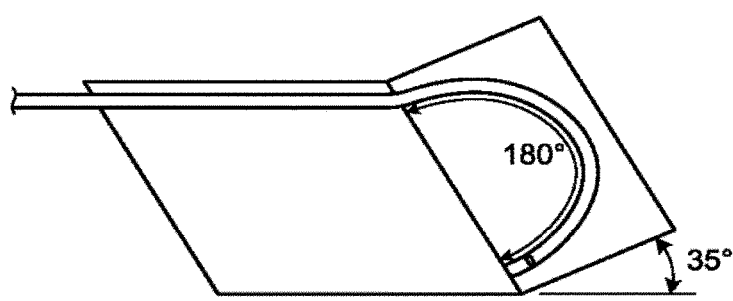
FIG. 11D is a diagram illustrating an example of the catheter according to the first embodiment.
Figure 12A:
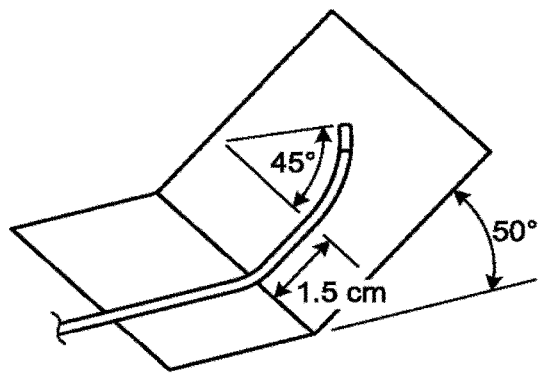
FIG. 12A is a diagram illustrating an example of the catheter according to the first embodiment.
Figure 12B:
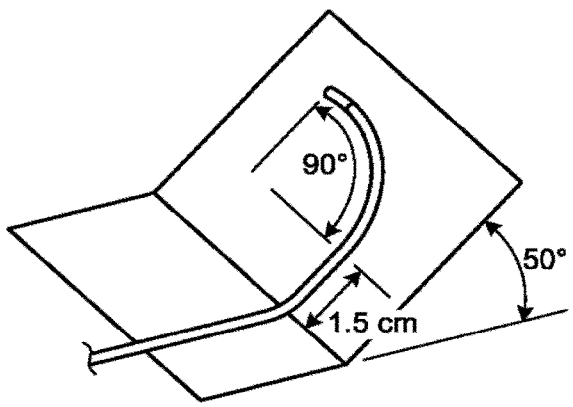
FIG. 12B is a diagram illustrating an example of the catheter according to the first embodiment.
Figure 12C:
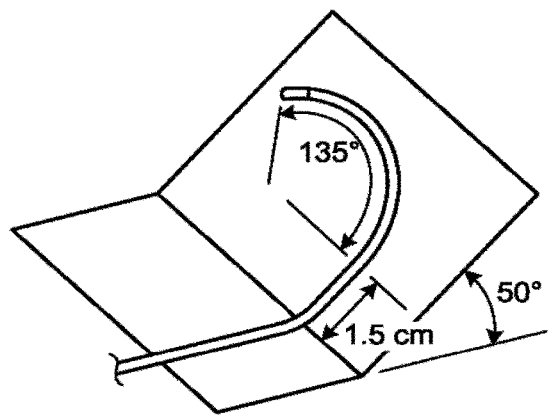
FIG. 12C is a diagram illustrating an example of the catheter according to the first embodiment.
Figure 12D:
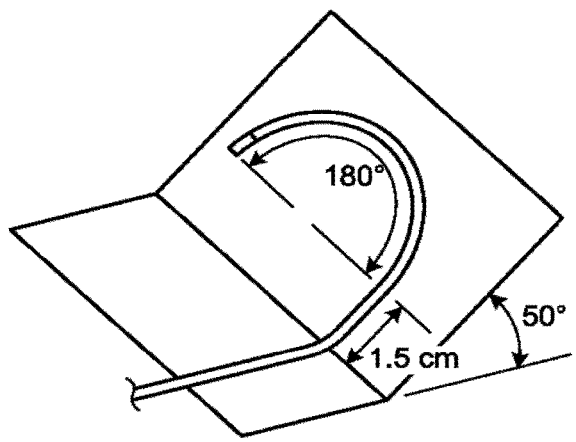
FIG. 12D is a diagram illustrating an example of the catheter according to the first embodiment.

The presentation function 444 may further select a catheter on the basis of the shape of the path, and present the selected catheter. For example, first, the presentation function 444 determines the number of joints included in the bendable catheter, on the basis of the shape of the path calculated with the calculation function 443. As an example, when the path calculated with the calculation function 443 is a two-dimensional curve on a plane, because a catheter with one joint can reach the treatment target region, the presentation function 444 sets the number of joints of the catheter to "1". In addition, as illustrated in FIG. 10, the presentation function 444 selects a catheter having a joint. FIG. 10 is a diagram illustrating an example of the catheter according to the first embodiment.

By contrast, when the path is not a two-dimensional curve on a plane (e.g., when the path is a three-dimensional curve), the presentation function 444 selects a catheter including a plurality of joints. The following is an explanation of a catheter including two joints having bending directions orthogonal to each other, as an example of the catheter including a plurality of joints.

First, catheters including two joints having bending directions orthogonal to each other are classified into two types. Specifically, supposing that the joint closer to the distal end of the catheter is a first joint and the other joint is a second joint, the two types include a type (such as catheters illustrated in FIG. 11A, FIG. 11B, FIG. 11C, and FIG. 11D) in which the second joint is bent in a direction rotated by "90°" clockwise from the bending direction of the first joint, as viewed from the distal end side of the catheter, and a type (such as catheters illustrated in FIG. 12A, FIG. 12B, FIG. 12C, and FIG. 12D) in which the second joint is bent in a direction rotated by "90°" counterclockwise from the bending direction of the first joint. FIG. 11A, FIG. 11B, FIG. 11C, FIG. 11D, FIG. 12A, FIG. 12B, FIG. 12C, and FIG. 12D are diagrams illustrating examples of the catheter according to the first embodiment.

For example, when the path has a shape puncturing the oval fossa from the right atrium side and further curving toward the back side of the subject P, the presentation function 444 selects one of the catheters illustrated in FIG. 11A, FIG. 11B, FIG. 11C, and FIG. 11D. By contrast, when the path has a shape puncturing the oval fossa from the right atrium side and further curving toward the abdomen side of the subject P, the presentation function 444 selects one of the catheters illustrated in FIG. 12A, FIG. 12B, FIG. 12C, and FIG. 12D.

In addition, the presentation function 444 selects a catheter according to the bending angle of the curve in the path in the left atrium. For example, when the path in the left atrium is slightly curved toward the back side of the subject P, because the bending angle of the first joint satisfies the requirement even when it is small, the presentation function 444 selects the catheter of FIG. 11A with a bending angle of "45°" of the first joint. As another example, the presentation function 444 selects one of the catheter of FIG. 11B with a bending angle of "90°" of the first joint, the catheter of FIG. 11C with a bending angle of "135°" of the first joint, and the catheter of FIG. 11D with a bending angle of "180°" of the first joint such that the bending angle of the first joint increases as the path in the left atrium is curved more widely toward the back side of the subject P. As another example, the presentation function 444 selects one of the catheters of FIG. 12A, FIG. 12B, FIG. 12C, and FIG. 12D such that the bending angle of the first joint increases as the path in the left atrium is curved more widely toward the abdomen side of the subject P.

The description above illustrates the case of selecting a catheter on the basis of the bending angle of the curve in the path in the left atrium, but the embodiment is not limited thereto. For example, the presentation function 444 may select a catheter, by determining a distance between the first joint and the second joint in accordance with the positions at which the curves occur in the path. As an example, when curves occur at a short interval in the path, the presentation function 444 selects a catheter having a short distance between the first joint and the second joint, as illustrated in FIG. 11A, FIG. 11B, FIG. 11C, and FIG. 11D. By contrast, when curves occur at an interval in the path, the presentation function 444 selects a catheter having a distance between the first joint and the second joint, as illustrated in FIG. 12A, FIG. 12B, FIG. 12C, and FIG. 12D.

After the catheter is selected, the presentation function 444 presents the selected catheter to the operator. For example, the presentation function 444 displays information, such as an image illustrating the selected catheter, the positions and the number of joints included in the catheter, the maximum values of the bending angles of the respective joints, the bending directions, and the curvature in bending, on the display 420. The control function 441 may receive an operation to determine whether to use the presented catheter for the operation from the operator. In addition, when the restriction relating to the bending angle of the medical device is changed by selection of the catheter, the calculation function 443 may further calculate the puncturing region, on the basis of the changed restriction relating to the bending angle of the medical device.

As described above, according to the first embodiment, the acquisition function 442 acquires CT image data indicating the heart of the subject P, and acquires the oval fossa region R1 corresponding to the oval fossa, and the target region R2 corresponding to the treatment target region, from the acquired CT image data. The calculation function 443 calculates the puncturing region, in the oval fossa region R1, enabling the medical device reaching the treatment target region through the oval fossa to reach the treatment target region without coming into contact with the internal wall of the left atrium on the basis of the oval fossa region R1 and the target region R2. The presentation function 444 presents the puncturing region. With this structure, the medical image processing apparatus 400 according to the first embodiment facilitates an operation accompanied with puncturing of the interatrial septum.

In addition, according to the first embodiment, the calculation function 443 further calculates the path of the medical device to reach the treatment target region through the oval fossa, and the presentation function 444 displays the puncturing region and the path on the CT image. With this structure, the medical image processing apparatus 400 according to the first embodiment assists the planning of the path of the medical device, and further facilitates an operation accompanied with puncturing of the interatrial septum.

In addition, according to the first embodiment, the presentation function 444 selects a catheter on the basis of the shape of the path of the medical device to reach the treatment target region through the oval fossa, and presents the selected catheter. With this structure, the medical image processing apparatus 400 according to the first embodiment assists selection of a catheter, and further facilitates the operation by enabling use of a proper catheter.

The first embodiment described above illustrates the case where the medical image processing apparatus 400 calculates and presents the puncturing region. By contrast, the second embodiment illustrates the case where the ultrasonic diagnostic apparatus 200 calculates and presents the puncturing region. The medical image processing system 1 according to the second embodiment has the same structure as that of the medical image processing system 1 illustrated in FIG. 1. The medical image processing system 1 according to the second embodiment may not include the medical image processing apparatus 400.

Figure 13:
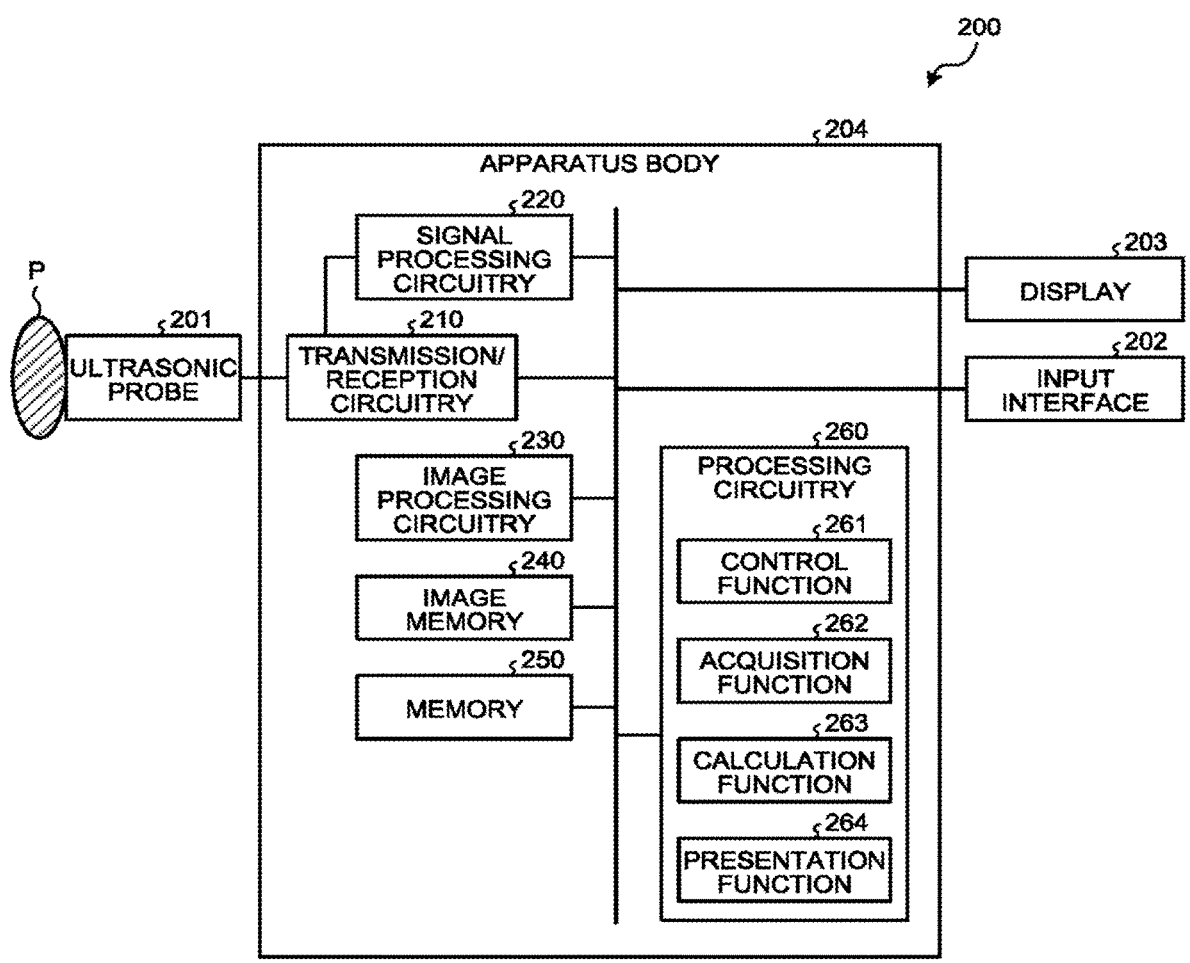
FIG. 13 is a block diagram illustrating an example of an ultrasonic diagnostic apparatus according to a second embodiment.

The following is an explanation of the ultrasonic diagnostic apparatus 200 according to the second embodiment, with reference to FIG. 13. FIG. 13 is a block diagram illustrating an example of the ultrasonic diagnostic apparatus 200 according to the second embodiment. As illustrated in FIG. 13, the ultrasonic diagnostic apparatus 200 according to the second embodiment includes an ultrasonic probe 201, an input interface 202, a display 203, and an apparatus body 204. The ultrasonic probe 201, the input interface 202, and the display 203 are connected with the apparatus body 204 such that they are capable of communicating with the apparatus body 204. The subject P is not included in the structure of the ultrasonic diagnostic apparatus 200.

The ultrasonic probe 201 transmits and receives ultrasonic waves. For example, the ultrasonic probe 201 includes a plurality of piezoelectric transducer elements (not illustrated). These piezoelectric transducer elements generate ultrasonic waves on the basis of a drive signal supplied from transmission/reception circuitry 210 included in the apparatus body 204 described later. The piezoelectric transducer elements included in the ultrasonic probe 201 receive reflected waves from the subject P and convert the waves into electric signals. The ultrasonic probe 201 also includes a matching layer (not illustrated) provided for the piezoelectric transducer elements, and a backing material (not illustrated) preventing backward transmission of ultrasonic waves from the piezoelectric transducer elements. The ultrasonic probe 201 is detachably connected with the apparatus body 204.

When ultrasonic waves are transmitted from the ultrasonic probe 201 to the subject P, the transmitted ultrasonic waves are successively reflected with a discontinuous surface of acoustic impedance in the tissue in the body of the subject P. The reflected waves are received as reflected wave signals with the piezoelectric transducer elements included in the ultrasonic probe 201. The amplitudes of the received reflected wave signals depend on a difference in acoustic impedance in the discontinuous surface with which the ultrasonic waves are reflected. A reflected wave signal in the case where the transmitted ultrasonic pulses are reflected with a surface of the moving blood flow or the wall of the heart or the like depends on the speed component of the moving element in the ultrasonic wave transmission direction by the Doppler effect, and is subjected to frequency shift.

For example, the ultrasonic probe 201 according to the second embodiment is a TEE probe. The ultrasonic probe 201 being a TEE probe is orally inserted into the body of the subject P, and caused to abut against the upper digestive tracts, such as the esophagus and the stomach. Thereafter, the ultrasonic probe 201 mechanically rotates a plurality of piezoelectric transducer elements, to image a desired cross section, and/or images three-dimensional ultrasonic image data (volume data). As another example, the ultrasonic probe 201 may be a two-dimensional array ultrasonic probe including a plurality of ultrasonic transducer elements arranged in a matrix manner, and capable of performing three-dimensional ultrasonic scan on the subject P. The two-dimensional array ultrasonic probe is capable of scanning the subject P electronically in a three-dimensional manner, by electronically focusing ultrasonic waves and transmitting and receiving the ultrasonic waves.

The input interface 202 includes a mouse, a keyboard, a trackball, a switch, a button, a joy stick, and/or a touch panel used by the operator for inputting various instructions and/or various settings, to transmit information of the instruction and/or the setting received from the operator to the apparatus body 204.

The display 203 displays a graphical user interface (GUI) for the user of the ultrasonic diagnostic apparatus 200 to input various setting requests using the input interface 202, the ultrasonic image imaged with the apparatus body 204, the CT image acquired from the X-ray CT apparatus 100, and the puncturing region calculated with a calculation function 263 and the like.

The apparatus body 204 generates ultrasonic image data on the basis of the reflective wave signal received with the ultrasonic probe 201. The ultrasonic image data generated with the apparatus body 204 may be two-dimensional ultrasonic image data generated on the basis of the two-dimensional reflective wave signals, or three-dimensional ultrasonic image data generated on the basis of the three-dimensional reflective wave signals.

As illustrated in FIG. 13, the apparatus body 204 includes the transmission/reception circuitry 210, signal processing circuitry 220, image processing circuitry 230, an image memory 240, a memory 250, and processing circuitry 260. The transmission/reception circuitry 210, the signal processing circuitry 220, the image processing circuitry 230, the image memory 240, the memory 250, and the processing circuitry 260 are connected such that they are capable of communicating with one another.

The transmission/reception circuitry 210 controls the transmission and reception of ultrasonic waves by the ultrasonic probe 201, on the basis of an instruction from the processing circuitry 260 that will be described later. The transmission/reception circuitry 210 includes a pulse generator (not illustrated), transmission delay circuitry (not illustrated), and a pulser (not illustrated), and supplies a drive signal to the ultrasonic probe 201. The pulse generator repeatedly generates rate pulses to form transmission ultrasonic waves at a predetermined pulse repetition frequency (PRF). The transmission delay circuitry converges ultrasonic waves generated from the ultrasonic probe 201 into a beam shape, and supplies each of the rate pulses generated with the pulse generator with delay time for each of the piezoelectric transducer elements necessary for determining the transmission directivity. The pulser applies a drive signal (drive pulse) to the ultrasonic probe 201 at a timing based on the rate pulses. Specifically, the transmission delay circuitry changes the delay time applied to each of the rate pulses, to adjust the transmission direction of the ultrasonic waves transmitted from the piezoelectric transducer element surface as desired.

The transmission/reception circuitry 210 is capable of instantly changing the transmission frequency and the transmission drive voltage and the like, to execute a predetermined scan sequence, on the basis of an instruction from the processing circuitry 260 that will be described later. In particular, change of the transmission drive voltage is achieved with transmission circuitry (not illustrated) of a linear-amplifier type capable of instantly switching the value, or a mechanism electrically switching a plurality of power units (not illustrated).

In addition, for example, the transmission/reception circuitry 210 includes amplifier circuitry (not illustrated), analog/digital (A/D) circuitry (not illustrated), an adder (not illustrated)), and phase detection circuitry (not illustrated), and performs various types of processing on the reflected wave signals received with the ultrasonic probe 201 to generate reflected wave data. The amplifier circuitry amplifies the reflective wave signals for each of channels to perform gain correction. The A/D converter performs A/D conversion on the gain-corrected reflected wave signals, and provides the digital data with delay time necessary for determining the reception directivity. The adder performs addition of the reflected wave signals processed with the A/D converter. Addition with the adder emphasizes the reflection component from the direction corresponding to the reception directivity of the reflected wave signal. The phase detection circuitry converts the output signal of the adder into an in-phase signal (I signal) of a base band and a quadrature-phase signal (Q signal). The phase detection circuitry transmits the I signal and the Q signal (IQ signal) to the signal processing circuitry 220. The data before processing with the phase detection circuitry is also referred to as "RF signal". In the following description, the "IQ signal and the RF signal" generated on the basis of the reflected waves of ultrasonic waves are referred to as "reflected wave data" together.

The signal processing circuitry 220 performs various types of image processing on the reflected wave data generated with the transmission/reception circuitry 210 from the reflected wave signal. The signal processing circuitry 220 performs logarithmic amplification, envelope detection, and/or logarithmic compression and the like on the reflected wave data (IQ signal) read from the buffer, to generate data (B mode data) in which signal intensities of multiple points are expressed with intensities of luminance.

In addition, the signal processing circuitry 220 performs frequency analysis on the reflected wave data, to generate data (Doppler data) obtained by extracting movement information based on the Doppler effect of a moving element positioned in the scanning range. Specifically, the signal processing circuitry 220 generates Doppler data obtained by estimating the average speed, the average dispersion value, and/or the average power value at each of a plurality of sample points, as the movement information of the moving element. The moving element is, for example, the blood flow, the tissue, such as the wall of the heart, and a contrast medium. The signal processing circuitry 220 according to the present embodiment generates Doppler data obtained by estimating the average speed of the blood flow, the average dispersion value of the blood flow, and/or the average power value of the blood flow, as the movement information (blood flow information) of the blood flow.

The image processing circuitry 230 generates ultrasonic image data from various types of data generated with the signal processing circuitry 220. The image processing circuitry 230 generates two-dimensional B mode image data in which intensities of reflected waves are expressed with luminance, from the two-dimensional B mode data generated with the signal processing circuitry 220. The image processing circuitry 230 also generates two-dimensional Doppler image data obtained by visualizing the blood flow information, from the two-dimensional Doppler data generated with the signal processing circuitry 220. The two-dimensional Doppler image data is speed image data, dispersed image data, power image data, or image data obtained by combining them. The image processing circuitry 230 generates color Doppler image data in which the blood flow information is displayed with colors, or Doppler image data in which one piece of blood flow information is displayed with a gray scale, as the Doppler image data.

The image processing circuitry 230 generally converts (scan convert) the scanning line signal column of ultrasonic scan into a scanning line signal column of a video format represented by televisions to generate ultrasonic image data. Specifically, the image processing circuitry 230 performs coordinate transformation in accordance with the ultrasonic wave scan form with the ultrasonic probe 201 to generate ultrasonic image data. The image processing circuitry 230 may perform various types of image processing, in addition to the scan convert. For example, the image processing circuitry 230 performs image processing (smoothing) by regenerating an average image of luminance using a plurality of image frames after scan conversion, and/or image processing (edge enhancement) using a differential filter in the image. The image processing circuitry 230 also combines character information of various parameters, a scale, and/or a body mark and the like with ultrasonic image data.

Specifically, the B mode data and the Doppler data serve as ultrasonic image data before scan conversion, and the data generated with the image processing circuitry 230 is ultrasonic image data after scan conversion. The B mode data and the Doppler data are also referred to as "raw data". The image processing circuitry 230 generates two-dimensional ultrasonic image data from two-dimensional ultrasonic image data before scan conversion.

In addition, the image processing circuitry 230 performs coordinate transformation on the three-dimensional B mode data generated with the signal processing circuitry 220 to generate three-dimensional B mode image data. The image processing circuitry 230 also performs coordinate transformation on the three-dimensional Doppler data generated with the signal processing circuitry 220 to generate three-dimensional Doppler image data.

In addition, the image processing circuitry 230 performs rendering on the volume data to generate various types of two-dimensional image data to display the volume data on the display 203. Examples of rendering performed with the image processing circuitry 230 include processing of performing multi planar reconstruction (MPR) to generate MPR image data from the volume data. Examples of rendering performed with the image processing circuitry 230 include volume rendering (VR) of generating two-dimensional image data reflecting three-dimensional information.

The image memory 240 is a memory storing ultrasonic image data generated with the image processing circuitry 230 therein. The image memory 240 is also capable of storing data generated with the signal processing circuitry 220 therein. The B mode data and the Doppler data stored in the image memory 240 can be invoked by the operator, for example, after imaging, and serves as ultrasonic image data through the image processing circuitry 230. The image memory 240 is also capable of storing reflected wave data output with the transmission/reception circuitry 210 therein.

The memory 250 stores control programs to perform ultrasonic transmission and reception, image processing, and display processing, diagnostic information (such as a patient ID and doctor's observations), and various types of data, such as a diagnostic protocol and various body marks, therein. The memory 250 is also used for storing image data stored in the image memory 240, if necessary. The data stored in the memory 250 can be transmitted to the external device through an interface (not illustrated). The memory 250 is also capable of storing data transmitted from the external device through an interface (not illustrated) therein. For example, the memory 250 stores CT image data transmitted from the X-ray CT apparatus 100 or the image storage apparatus 300 therein.

The processing circuitry 260 controls the whole processing performed with the ultrasonic diagnostic apparatus 200. Specifically, the processing circuitry 260 controls processing performed with the transmission/reception circuitry 210, the signal processing circuitry 220, and the image processing circuitry 230, on the basis of various setting requests input by the operator through the input interface 202, and the various control programs and various data read from the memory 250.

The processing circuitry 260 also performs control to display the ultrasonic image data stored in the image memory 240 and/or the memory 250 on the display 203, as a display ultrasonic image. For example, the processing circuitry 260 displays color Doppler image data generated with the image processing circuitry 230 on the display 203, as a display color Doppler image. In addition, for example, the processing circuitry 260 displays B mode image data generated with the image processing circuitry 230 on the display 203, as a display B mode image.

The processing circuitry 260 executes a control function 261, an acquisition function 262, a calculation function 263, and a presentation function 264. For example, the processing circuitry 260 reads a computer program corresponding to the control function 261 from the memory 250 and executes the computer program, to control processing performed with the transmission/reception circuitry 210, the signal processing circuitry 220 and the image processing circuitry 230, and receive various instructions and settings from the operator through the input interface 202.

In addition, for example, the processing circuitry 260 reads a computer program corresponding to the acquisition function 262 from the memory 250 and executes the computer program, to acquire CT image data from the X-ray CT apparatus 100 or the image storage apparatus 300, and acquire the oval fossa region R1 corresponding to the oval fossa and the target region R2 corresponding to the treatment target region from the CT image data. For example, the processing circuitry 260 also reads computer programs corresponding to the calculation function 263 and the presentation function 264 from the memory 250 and executes the computer programs to calculate the puncturing region to be punctured with the medical device in the interatrial septum of the subject P, and present the calculated puncturing region to the operator. The acquisition function 262, the calculation function 263, and the presentation function 264 are capable of executing the same processing as the acquisition function 442, the calculation function 443, and the presentation function 444, respectively.

In the ultrasonic diagnostic apparatus 200 illustrated in FIG. 13, each of the processing functions is stored in the memory 250, in the form of a computer program executable with a computer. The transmission/reception circuitry 210, the signal processing circuitry 220, the image processing circuitry 230, and the processing circuitry 260 are processors reading respective computer programs from the memory 250 and executing the computer programs to achieve the functions corresponding to the respective computer programs. FIG. 13 illustrates that the single processing circuitry 260 achieves the control function 261, the acquisition function 262, the calculation function 263, and the presentation function 264, but a plurality of independent processors may be combined to form the processing circuitry 260, and the processors may execute the respective computer programs to achieve the functions.

With the structure described above, the ultrasonic diagnostic apparatus 200 according to the second embodiment facilitates an operation accompanied with puncturing of the interatrial septum. Specifically, first, the acquisition function 262 acquires CT image data from the X-ray CT apparatus 100 or the image storage apparatus 300. Thereafter, the acquisition function 262 acquires the oval fossa region R1 corresponding to the oval fossa, and the target region R2 corresponding to the treatment target region, from the CT image data indicating the heart of the subject P. For example, the acquisition function 442 acquires the oval fossa region R1 from the CT image data by segmentation. In addition, for example, in treatment of mitral insufficiency, the acquisition function 262 acquires an operation to designate a location to be clipped with a clip in the mitral valve from the operator to acquire the target region R2.

Thereafter, the calculation function 263 calculates the puncturing region enabling the medical device to reach the treatment target region without coming into contact with the internal wall of the left atrium of the subject P, in the oval fossa region R1, on the basis of the oval fossa region R1 and the target region R2. For example, first, the calculation function 263 calculates height "h" from the target region R2 to a region R3 corresponding to the upper part of the left atrium, and adjusts the puncturing region in the oval fossa region R1, on the basis of the height "h". Thereafter, the calculation function 263 generates a line L5 connecting the target region R2 with the inferior vena cava region R4, and further adjusts the puncturing region in the oval fossa region R1 on the basis of the generated line L5.

Thereafter, the presentation function 264 presents the puncturing region calculated with the calculation function 263. For example, the presentation function 264 displays the puncturing region on the ultrasonic image imaged under the control of the control function 261. As an example, first, the ultrasonic probe 201 serving as a TEE probe scans the region including the heart of the subject P, in the state where the ultrasonic probe 201 orally abuts against the upper digestive tracts. Thereafter, the control function 261 controls the transmission/reception circuitry 210, to perform various types of processing on the reflected wave signal received with the ultrasonic probe 201 and generates reflected wave data. Thereafter, the control function 261 controls the signal processing circuitry 220, to perform logarithmic amplification, envelope detection, and/or logarithmic compression and the like on the reflected wave data, to generate B mode data. Thereafter, the control function 261 controls the image processing circuitry 230, to generate B mode image data, in which intensities of the reflected waves are expressed with luminance, from the B mode data. The presentation function 264 displays the B mode image data as a display B mode image on the display 203, and displays the puncturing region calculated with the calculation function 263 on the B mode image. When the medical device has been inserted into the subject P, the presentation function 264 can present positional relation between the medical device and the puncturing region to the operator, in the B mode image.

The operator who has referred to the B mode image performs an operation using the medical device. Specifically, first, the guide wire is inserted from the femoral vein of the subject P, and reaches the right atrium of the subject P. Thereafter, the catheter reaches the right atrium of the subject P along the preceding guide wire. Thereafter, the needle runs through the inside of the catheter to reach the right atrium of the subject P and punctures the puncturing region in the oval fossa. Thereafter, the guide wire is inserted into the left atrium from the position punctured with the needle. Thereafter, the catheter reaches the left atrium of the subject P along the preceding guide wire.

Thereafter, the clip reaches the left atrium of the subject P through the inside of the catheter. For example, after the catheter reaches the left atrium, the clip reaches the left atrium of the subject P through the inside of the catheter, and is held at the distal end position of the catheter. Thereafter, the catheter is bent in accordance with an instruction of the operator. In this manner, the clip at the distal end position of the catheter moves to the treatment target region. Thereafter, the clip clips two valves forming the mitral valve to bring them to into contact with each other.

In this operation, the operator can determine the position of the clip, on the basis of the ultrasonic image. For example, first, the control function 261 controls the signal processing circuitry 220, to perform frequency analysis on the reflected wave data, and generates Doppler data based on the Doppler effect of the moving element positioned in the scanning range. Thereafter, the control function 261 controls the image processing circuitry 230, to generate two-dimensional Doppler image data obtained by visualizing the blood flow information, from the Doppler data. For example, the control function 261 generates color Doppler image data in which the blood flow information is displayed with colors, as the Doppler image data. The presentation function 264 displays the color Doppler image data as a display color Doppler image on the display 203. This structure enables the operator to judge whether backflow of the blood is sufficiently relieved by clipping. When the operator judges that backflow is not sufficiently relieved, the operator can change position of the clip. After the position of the clip is determined, the clip is separated from the medical device, and indwelled at the distal end of the mitral valve.

The first and the second embodiments have been described above, but embodiments may be carried out in various different forms other than the embodiments described above.

For example, the processing circuitry 440 or the processing circuitry 260 described above may further include a notification function for determining whether the medical device is coming into contact with the heart of the subject P, and performing notification in advance when it determines that the medical device is coming into contact with the heart. As an example, first, the notification function acquires information indicating the position and the movement of the medical device. The information indicating the position and the movement of the medical device is information indicating the position and the movement of the medical device inserted into the body of the subject P with respect to the subject P. For example, after the medical device is inserted into the heart of the subject P, the notification function acquires information indicating the position and the movement of the medical device, on the basis of the medical device drawn on the X-ray image or the ultrasonic image obtained by actually imaging the region including the heart of the subject P. In addition, for example, the notification function acquires information indicating the position and the movement of the medical device, on the basis of a sensor provided on the medical device and indicating the position thereof.

Thereafter, the notification function determines whether the medical device is coming into contact with the heart of the subject P, on the basis of the information indicating the position and the movement of the medical device. For example, the notification function determines that the medical device is coming into contact with the heart of the subject P, when the medical device comes into contact with the internal wall of the left atrium within "one second" by moving at the actually acquired speed from the actually acquired position. The notification function notifies the operator that the medical device will come in contact with the heart, before the medical device is coming in contact with the heart of the subject P. For example, the notification function notifies the operator that the medical device will come into contact with the heart of the subject P, with a display on the display 420 or the display 203 and/or sound. The notification function may perform no notification, when the medical device comes in contact with the puncturing region in the heart of the subject P.

The embodiments described above illustrate the case of calculating the puncturing region in the oval fossa region.

However, the embodiments are not limited thereto. For example, the processing circuitry 440 or the processing circuitry 260 may calculate the puncturing region in the interatrial septum, without being limited to the oval fossa region.

Specifically, first, the processing circuitry 440 or the processing circuitry 260 acquires the position of the interatrial septum and the target region corresponding to the treatment target region, in the CT image data. Thereafter, the processing circuitry 440 or the processing circuitry 260 calculates the puncturing region enabling the medical device to reach the treatment target region through the interatrial septum, in the interatrial septum, on the basis of the position of the interatrial septum and the target region. The processing circuitry 440 or the processing circuitry 260 may calculate the puncturing region in a part of the interatrial septum other than the oval fossa region. Thereafter, the processing circuitry 440 or the processing circuitry 260 presents the calculated puncturing region.

The embodiments described above illustrate the target region corresponding to the treatment target region, as an example of the device reaching position. However, the embodiments are not limited thereto. For example, the processing circuitry 440 or the processing circuitry 260 may calculate the puncturing region, with the position other than the target region serving as the device reaching position.

As an example, in inspection using a medical device, such as an endoscope and an ultrasonic probe, the medical device is disposed at a position distant from the treatment target region to perform imaging (scan) of the treatment target region. As another example, in a treatment method of ejecting a chemical agent from the medical device, such as a catheter, to the treatment target region, the medical device is disposed in an upstream position of the treatment target region, to execute treatment for the treatment target region. In such a case, the treatment target region is different from the device reaching position.

For example, first, the processing circuitry 440 or the processing circuitry 260 acquires the position of the interatrial septum and the device reaching position in the CT image data. In this operation, the processing circuitry 440 or the processing circuitry 260 may acquire the device reaching position by image processing on the CT image data, or receive an operation to designate the device reaching position on the CT image data from the operator.

As another example, the processing circuitry 440 or the processing circuitry 260 may specify the device reaching position, on the basis of information of the medical device. As an example, the processing circuitry 440 or the processing circuitry 260 specifies the device reaching position, on the basis of the size of the medical device, in left atrial appendage closure. Specifically, when the left atrial appendage with a conical shape is closed, it is required to indwell the medical device at a position at which the internal diameter of the left atrial appendage is made smaller, as the size of the umbrella-shaped medical device used for closure is smaller. Specifically, it is required to indwell the medical device in a deeper position of the left atrial appendage, as the size of the medical device is smaller. Accordingly, the processing circuitry 440 or the processing circuitry 260 specifies the indwelling position corresponding to the size of the umbrella-shaped medical device used in left atrial appendage closure, as the device reaching position.

Thereafter, the processing circuitry 440 or the processing circuitry 260 calculates the puncturing region enabling the medical device to reach the device reaching position through the interatrial septum, in the interatrial septum, on the basis of the position of the interatrial septum and the device reaching position. Thereafter, the processing circuitry 440 or the processing circuitry 260 presents the calculated puncturing region.

In addition, the embodiments described above illustrate the medical image processing apparatus 400 including the processing circuitry 440, or the ultrasonic diagnostic apparatus 200 including the processing circuitry 260. However, the embodiments are not limited thereto. For example, processing circuitry included in the X-ray CT apparatus 100 illustrated in FIG. 1 may include functions corresponding to the acquisition function 442, the calculation function 443, and the presentation function 444. In addition, for example, the medical image processing system 1 may include an X-ray diagnostic apparatus instead of the ultrasonic diagnostic apparatus 200, and processing circuitry included in the X-ray diagnostic apparatus may include functions corresponding to the acquisition function 442, the calculation function 443, and the presentation function 444. Specifically, any medical image diagnostic apparatus included in the medical image processing system 1 may achieve the same processing as the processing performed with the processing circuitry 440.

The term "processor" used in the explanation described above means, for example, a central processing unit (CPU), a graphics processing unit (GPU), or a circuit, such as an application specific integrated circuit (ASIC) and a programmable logic device (such as a simple programmable logic device (SPLD), a complex programmable logic device (CPLD), and a field programmable gate array (FPGA)). The processor achieves a function by reading a computer program stored in a memory and executing the computer program. Instead of storing a computer program in a memory, a computer program may be directly incorporated in a circuit of the processor. In this case, the processor achieves its function by reading and executing a computer program incorporated in the circuit. Each of the processors in the embodiments is not limited to the case of being configured as a single circuit for each processor, but a plurality of independent circuits may be combined as a processor to achieve the function thereof. In addition, a plurality of constituent elements may be integrated into a processor to achieve the function thereof.

The constituent elements of the apparatuses according to the first to the second embodiments are functional and conceptual ones, and do not always require being physically configured as illustrated. Specifically, the specific form of distribution and integration of each of the apparatuses is not limited to illustrated one, but all or part thereof may be functionally or physically distributed or integrated in desired unit according to various loads and/or situations of use. In addition, all or any part of each of the processing functions performed in each of the apparatuses may be achieved with a CPU or a computer program analyzed and executed with the CPU, or achieved as hardware by wired logic.

The control methods explained in the first to the second embodiments may be achieved by executing a prepared image processing program with a computer, such as a personal computer and a work station. The image processing program can be distributed through a network, such as the Internet. In addition, the image processing program may be recorded on a computer-readable recording medium, such as a hard disk, a flexible disk (FD), a CD-ROM, a MO, and a DVD, and executed by being read from the recording medium with a computer.

At least one of the embodiments explained above facilitates an operation accompanied with puncturing of the interatrial septum.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus comprising processing circuitry configured to:
    acquire an oval fossa region corresponding to an oval fossa, a target region corresponding to a treatment target region and an inferior vena cava region corresponding to an inferior vena cava in a medical image indicating the heart of a subject;
    calculate a puncturing region, in the oval fossa region, enabling a medical device to reach the treatment target region through the oval fossa region without coming into contact with an internal wall of a left atrium on a basis of the oval fossa region and the target region; and
    present the puncturing region on a display image indicating an interatrial septum, wherein the processing circuitry is further configured to determine whether the medical device is able to reach the treatment target region according to whether each of a plurality of positions of the oval fossa region is included in a plurality of planes, the plurality of planes including the target region and a plurality of straight lines parallel with a core line of the inferior vena cava region and running through the inferior vena cava region.

2. The medical image processing apparatus according to claim 1, wherein the puncturing region is set to a position enabling the medical device to reach the target region and preventing the medical device from coming into contact with a contact-prohibited region set to at least a part of the heart.

3. The medical image processing apparatus according to claim 1, wherein the processing circuitry is further configured to:
    acquire device information relating to a movable range of the medical device; and
    calculate the puncturing region in the oval fossa region on a basis of the device information, in addition to the oval fossa region and the target region.

4. The medical image processing apparatus according to claim 3, wherein the processing circuitry is configured to:
    acquire information relating to restriction relating to a bending angle of the medical device, as the device information; and
    determine whether the medical device is able to reach the target region when the medical device is caused to reach the target region by being bent in the left atrium, on the basis of the restriction relating to the bending angle of the medical device and positional relation between the oval fossa region and the target region.

5. The medical image processing apparatus according to claim 1, wherein the processing circuitry is configured to determine whether the medical device is coming into contact with the internal wall of the left atrium on a basis of height from the target region to a region corresponding to an upper part of the left atrium.

6. The medical image processing apparatus according to claim 1, wherein the processing circuitry is further configured to:
    acquire an aortic region corresponding to an aorta from the medical image; and
    calculate the puncturing region in a region in the oval fossa region having a distance equal to or larger than a threshold from the aortic region.

7. The medical image processing apparatus according to claim 6, wherein the processing circuitry is further configured to present a region having a distance equal to or smaller than a threshold from the aortic region.

8. The medical image processing apparatus according to claim 1, wherein the processing circuitry is further configured to:
    acquire a thickness for each of positions in the oval fossa region from the medical image; and
    calculate the puncturing region in a region in the oval fossa region having the thickness equal to or smaller than a threshold.

9. The medical image processing apparatus according to claim 8, wherein
    the medical device includes a puncture needle used for puncturing the oval fossa, and
    the processing circuitry is further configured to select a puncture needle on a basis of the thickness in the puncturing region, and present the selected puncture needle.

10. The medical image processing apparatus according to claim 1, wherein the processing circuitry is configured to display the puncturing region on an X-ray image or an ultrasonic image obtained by actually imaging a region including the heart of the subject.

11. The medical image processing apparatus according to claim 1, wherein the processing circuitry is further configured to:
    calculate a path of the medical device to reach the target region through the oval fossa; and
    display the puncturing region and the path on the medical image.

12. The medical image processing apparatus according to claim 11, wherein the processing circuitry is further configured to display a position of the medical device on the medical image.

13. The medical image processing apparatus according to claim 11, wherein
    the medical device includes a bendable catheter, and
    the processing circuitry is further configured to select a catheter on a basis of a shape of the path, and present the selected catheter.

14. The medical image processing apparatus according to claim 1, wherein the processing circuitry is further configured to determine whether the medical device is coming into contact with the heart excluding the puncturing region on a basis of information indicating a position and movement of the medical device, and perform notification in advance when the processing circuitry determines that the medical device is coming into contact with the heart.

15. The medical image processing apparatus according to claim 2, wherein the processing circuitry is further configured to:
    acquire device information relating to a movable range of the medical device; and calculate the puncturing region in the oval fossa region on a basis of the device information, in addition to the oval fossa region and the target region.

16. The medical image processing apparatus according to claim 3, wherein
the processing circuitry is configured to calculate the puncturing region, in the oval fossa region, enabling the medical device reaching the treatment target region through the oval fossa region to reach the treatment target region without coming into contact with an internal wall of a left atrium on the basis of the oval fossa region and the target region.

17. A medical image diagnostic apparatus comprising processing circuitry configured to:
acquire an oval fossa region corresponding to an oval fossa, a target region corresponding to a treatment target region and an inferior vena cava region corresponding to an inferior vena cava in a medical image indicating the heart of a subject;
calculate a puncturing region, in the oval fossa region, enabling a medical device to reach the treatment target region through the oval fossa region without coming into contact with an internal wall of a left atrium on a basis of the oval fossa region and the target region; and
present the puncturing region on a display image indicating an interatrial septum, wherein the processing circuitry is further configured to determine whether the medical device is able to reach the treatment target region according to whether each of a plurality of positions of the oval fossa region is included in a plurality of planes, the plurality of planes including the target region and a plurality of straight lines parallel with a core line of the inferior vena cava region and running through the inferior vena cava region.

18. A medical image processing method comprising:
acquiring an oval fossa region corresponding to an oval fossa, a target region corresponding to a treatment target region and an inferior vena cava region corresponding to an inferior vena cava in a medical image indicating the heart of a subject;
calculating a puncturing region, in the oval fossa region, enabling a medical device to reach the treatment target region through the oval fossa region without coming into contact with an internal wall of a left atrium on a basis of the oval fossa region and the target region; and
presenting the puncturing region on a display image indicating an interatrial septum, wherein the calculating the puncturing region includes determining whether the medical device is able to reach the treatment target region according to whether each of a plurality of positions of the oval fossa region is included in a plurality of planes, the plurality of planes including the target region and a plurality of straight lines parallel with a core line of the inferior vena cava region and running through the inferior vena cava region.

19. The medical image processing apparatus according to claim 1, wherein the processing circuitry is further configured to:
generate a second plurality of lines for each of the straight lines connecting the target region and the inferior vena cava region;
determine a plurality of intersection points between the second plurality of lines and the oval fossa region; and
determine the puncturing region to be between the intersection points.

* * * * *